(12) United States Patent
Mitsuhashi

(10) Patent No.: US 9,458,496 B2
(45) Date of Patent: Oct. 4, 2016

(54) METHOD OF CHARACTERIZING VASCULAR DISEASES

(71) Applicants: Hitachi Chemical Co., Ltd., Tokyo (JP); Hitachi Chemical Research Center, Inc., Irvine, CA (US)

(72) Inventor: Masato Mitsuhashi, Irvine, CA (US)

(73) Assignees: HITACHI CHEMICAL COMPANY, LTD., Tokyo (JP); HITACHI CHEMICAL RESEARCH CENTER, INC., Irvine, CA (US)

( * ) Notice: Subject to any disclaimer, the term of this patent is extended or adjusted under 35 U.S.C. 154(b) by 238 days.

(21) Appl. No.: 13/710,192

(22) Filed: Dec. 10, 2012

(65) Prior Publication Data

US 2013/0089855 A1  Apr. 11, 2013

Related U.S. Application Data

(63) Continuation-in-part of application No. PCT/US2011/040015, filed on Jun. 10, 2011.

(60) Provisional application No. 61/354,117, filed on Jun. 11, 2010.

(51) Int. Cl.
 *C12Q 1/68* (2006.01)

(52) U.S. Cl.
 CPC .......... *C12Q 1/6809* (2013.01); *C12Q 1/6883* (2013.01); *C12Q 2600/158* (2013.01); *C12Q 2600/178* (2013.01)

(58) Field of Classification Search
 CPC .................................................. C12Q 1/6851
 USPC ........................................... 435/6, 6.1, 6.12
 See application file for complete search history.

(56) References Cited

U.S. PATENT DOCUMENTS

| | | | |
|---|---|---|---|
| 3,583,627 A | 6/1971 | Wilson | |
| 4,895,706 A | 1/1990 | Root et al. | |
| 4,925,572 A * | 5/1990 | Pall | 210/767 |
| 5,647,990 A | 7/1997 | Vassarotti | |
| 5,747,256 A | 5/1998 | Yan et al. | |
| 6,329,179 B1 * | 12/2001 | Kopreski | 435/91.2 |
| 6,964,850 B2 * | 11/2005 | Bevilacqua et al. | 435/6.11 |
| 7,741,023 B2 | 6/2010 | Mitsuhashi | |
| 7,745,180 B2 | 6/2010 | Mitsuhashi | |
| 2003/0203453 A1 | 10/2003 | Leonard | |
| 2004/0029124 A1 * | 2/2004 | Zohlnhofer et al. | 435/6 |
| 2004/0072193 A1 * | 4/2004 | Mitsuhashi | 435/6 |
| 2004/0203037 A1 * | 10/2004 | Lo et al. | 435/6 |
| 2004/0258570 A1 | 12/2004 | Beebe et al. | |
| 2004/0265864 A1 * | 12/2004 | Mitsuhashi | 435/6 |
| 2006/0144790 A1 | 7/2006 | Kelly et al. | |
| 2007/0254351 A1 * | 11/2007 | Abrignani et al. | 435/235.1 |
| 2008/0009009 A1 * | 1/2008 | Mitsuhashi | 435/6 |
| 2008/0015162 A1 | 1/2008 | Bhanot et al. | |
| 2008/0188816 A1 | 8/2008 | Shimazaki et al. | |
| 2008/0268429 A1 * | 10/2008 | Pietrzkowski | 435/6 |
| 2009/0011410 A1 * | 1/2009 | Mitsuhashi | 435/6 |
| 2009/0023149 A1 * | 1/2009 | Knudsen | 435/6 |
| 2009/0111128 A1 * | 4/2009 | Mitsuhashi | 435/7.24 |
| 2009/0149333 A1 * | 6/2009 | Knudsen et al. | 506/7 |
| 2009/0258379 A1 | 10/2009 | Klein et al. | |
| 2010/0113290 A1 * | 5/2010 | Klass et al. | 435/6 |
| 2010/0196426 A1 | 8/2010 | Skog et al. | |
| 2010/0203529 A1 | 8/2010 | Kuslich et al. | |
| 2012/0211566 A1 | 8/2012 | Hensel et al. | |
| 2013/0089864 A1 | 4/2013 | Mitsuhashi et al. | |
| 2013/0172208 A1 | 7/2013 | Mitsuhashi | |
| 2013/0337462 A1 | 12/2013 | Mergemeier | |
| 2014/0099649 A1 | 4/2014 | Mitsuhashi | |

FOREIGN PATENT DOCUMENTS

| | | | | |
|---|---|---|---|---|
| WO | WO2006045053 | * | 4/2006 | |
| WO | WO2008092993 | | 8/2008 | |
| WO | WO2009015357 | * | 1/2009 | ............... C12Q 1/68 |
| WO | WO2009057695 | | 5/2009 | |
| WO | WO2009100029 | | 8/2009 | |
| WO | WO2010056337 | * | 5/2010 | ............... C12Q 1/68 |
| WO | WO2010086163 | * | 8/2010 | ........... A61K 39/395 |
| WO | WO 2011/100458 | | 8/2011 | |
| WO | WO 2011/156734 | | 12/2011 | |
| WO | WO2011156763 | | 12/2011 | |
| WO | WO 2014/055687 | | 4/2014 | |
| WO | WO 2014/182330 | | 11/2014 | |

OTHER PUBLICATIONS

Arteaga, R. B., Chirinos, J. A., Soriano, A. O., Jy, W. et al., Endothelial microparticles and platelet and leukocyte activation in patients with the metabolic syndrome. Am. J. Cardiol. 2006, 98, 70-74.*

Bachmann, S., Mutig, K., Bates, J., Welker, P. et al., Renal effects of Tamm-Horsfall protein (uromodulin) deficiency in mice. Am. J. Physiol. Renal Physiol. 2005, 288, F559-567.*

Chen C, Skog J, Hsu CH, Lessard RT, Balaj L, Wurdinger T, Carter BS, Breakefield XO, Toner M, Irimia D. Microfluidic isolation and transcriptome analysis of serum microvesicles. Lab Chip. Feb. 21, 2010;10(4):505-11. Epub Dec. 8, 2009.*

Cheruvanky, A., Zhou, H., Pisitkun, T., Kopp, J. B. et al., Rapid isolation of urinary exosomal biomarkers using a nanomembrane ultrafiltration concentrator. Am. J. Physiol. Renal Physiol. 2007, 292, F1657-1661.*

(Continued)

*Primary Examiner* — Angela M Bertagna
*Assistant Examiner* — Olayinka Oyeyemi
(74) *Attorney, Agent, or Firm* — Knobbe Martens Olson & Bear LLP

(57) ABSTRACT

Embodiments of the invention relate generally to methods of diagnosing diseases and measuring homeostatic states. In particular, the methods described here are used to characterize RNA from vesicles for expression of disease related markers. Embodiments of the invention also relate generally to the characterization of RNA by using sensitive techniques such as PCR to internally sample organ health using whole blood.

14 Claims, 3 Drawing Sheets

(56) References Cited

OTHER PUBLICATIONS

Conde-Vancells J, Rodriguez-Suarez E, Gonzalez E, Berisa A, Gil D, Embade N, Valle M, Luka Z, Elortza F, Wagner C, Lu SC, Mato JM, Falcon-Perez M. Candidate biomarkers in exosome-like vesicles purified from rat and mouse urine samples. Proteomics Clin. Appl. Apr. 2010;4(4):416-25.*

Dennis JL, Vass JK, Wit EC, Keith WN, Oien KA. Identification from public data of molecular markers of adenocarcinoma characteristic of the site of origin. Cancer Res. Nov. 1, 2002; 62(21):5999-6005.*

Enard et al. Intra- and interspecific variation in primate gene expression patterns. Science. 2002. 296(5566):340-3.*

Gonzales PA, Pisitkun T, Hoffert JD, Tchapyjnikov D, Star RA, Kleta R, Wang NS, Knepper MA. Large-scale proteomics and phosphoproteomics of urinary exosomes. J Am Soc Nephrol. Feb. 2009;20(2):363-79. Epub Dec. 3, 2008.*

Guo X, Lin HM, Lin Z, Montaño M, Sansores R, Wang G, DiAngelo S, Pardo A, Selman M, Floros J. Surfactant protein gene A, B, and D marker alleles in chronic obstructive pulmonary disease of a Mexican population. Eur Respir J. Sep. 2001;18(3):482-90.*

Hoorn, E. J., Pisitkun, T., Zietse, R., Gross, P. et al., Prospects for urinary proteomics: exosomes as a source of urinary biomarkers. Nephrology (Carlton) 2005, 10, 283-290.*

Hunter, M. P., Ismail, N., Zhang, X., Aguda, B. D. et al., Detection of microRNA expression in human peripheral blood microvesicles. PLoS One 2008, 3, e3694.*

Koga K et al. Purification, characterization and biological significance of tumor-derived exosomes. Anticancer Res. Nov.-Dec. 2005; 25(6A):3703-7.*

Lucendo et al. Treatment with topical steroids downregulates IL-5, eotaxin-1/CCL11, and eotaxin-3/CCL26 gene expression in eosinophilic esophagitis. Am J Gastroenterol. 2008. 103(9):2184-93.*

Luo Yet al. RANTES stimulates inflammatory cascades and receptor modulation in murine astrocytes. Glia. Jul. 2002; 39(1):19-30.*

Mitchell PJ, Welton J, Staffurth J, Court J, Mason MD, Tabi Z, Clayton A. Can urinary exosomes act as treatment response markers in prostate cancer? J Transl Med. Jan. 12, 2009;7:4.*

Miranda KC, Bond DT, McKee M, Skog J, Paunescu TG, Da Silva N, Brown D, Russo LM. Nucleic acids within urinary exosomes/microvesicles are potential biomarkers for renal disease. Kidney Int. Jul. 2010; 78(2):191-9. Epub Apr. 28, 2010.*

Nilsson, J., Skog, J., Nordstrand, A., Baranov, V. et al., Prostate cancer-derived urine exosomes: a novel approach to biomarkers for prostate cancer. Br. J. Cancer 2009, 100, 1603-1607.*

Olszewska-Pazdrak B, Casola A, Saito T, Alam R, Crowe SE, Mei F, Ogra PL, Garofalo RP. Cell-specific expression of Rantes, MCP-1, and MIP-1 alpha by lower airway epithelial cells and eosinophils infected with respiratory syncytial virus. J Virol. Jun. 1998; 72(6):4756-64.*

Pisitkun T, Shen RF, Knepper MA. Identification and proteomic profiling of exosomes in human urine. Proc Natl Acad Sci USA. 2004; 101:13368-13373.*

Pisitkun T, Johnstone R, Knepper MA. Discovery of urinary biomarkers. Mol Cell Proteomics. Oct. 2006; 5(10):1760-71. Epub Jul. 12, 2006. Review.*

Post et al. Demonstration of the presence of independent pre-osteoblastic and pre-adipocytic cell populations in bone marrow-derived mesenchymal stem cells. Bone. Jul. 2008; 43(1):32-9. Epub Mar. 30, 2008.*

Rappa, G., Fodstad, O., Lorico, A., The stem cell-associated antigen CD133 (Prominin-1) is a molecular therapeutic target for metastatic melanoma. Stem Cells 2008, 26, 3008-3017.*

Sellam et al. Increased levels of circulating microparticles in primary Sjögren's syndrome, systemic lupus erythematosus and rheumatoid arthritis and relation with disease activity. Arthritis Res Ther. 2009;11(5):R156.*

Simpson RJ, Jensen SS, Lim JW. Proteomic profiling of exosomes: current perspectives. Proteomics. Oct. 2008; 8(19):4083-99. Review.*

Smalley, D. M., Sheman, N. E., Nelson, K., Theodorescu, D., Isolation and identification of potential urinary microparticle biomarkers of bladder cancer. J. Proteome Res. 2008, 7, 2088-2096.*

Taylor DD, Gercel-Taylor C. MicroRNA signatures of tumor-derived exosomes as diagnostic biomarkers of ovarian cancer. Gynecol Oncol. Jul. 2008;110(1):13-21.*

Thery et al. Isolation and characterization of exosomes from cell culture supernatants and biological fluids. Chapter 3. Curr. Protoc. Cell Biol. 2006 Unit 3.22.*

Tockman MS, Gupta PK, Pressman NJ, Mulshine JL. Considerations in bringing a cancer biomarker to clinical application. Cancer Res. May 1, 1992;52(9 Suppl):2711s-2718s. Review.*

Vaes et al. Comprehensive microarray analysis of bone morphogenetic protein 2-induced osteoblast differentiation resulting in the identification of novel markers for bone development. J Bone Miner Res. 2002. 17(12):2106-18.* van Niel G, Porto-Carreiro I, Simoes S, Raposo G. Exosomes: a common pathway for a specialized function. J Biochem. Jul. 2006;140(1):13-21. Review.* van't Veer LJ, Bernards R. Enabling personalized cancer medicine through analysis of gene-expression patterns. Nature. Apr. 3, 2008;452(7187):564-70.*

Whitehead A, Crawford DL. Variation in tissue-specific gene expression among natural populations. Genome Biol. 2005;6(2):R13. Epub Jan. 26, 2005.*

Xu et al. Gene expression in peripheral blood differs after cardioembolic compared with large-vessel atherosclerotic stroke: biomarkers for the etiology of ischemic stroke. J Cereb Blood Flow Metab. Jul. 2008;28(7):1320-8. Epub Apr. 2, 2008.*

Bio Scientific, ExoMir Kit Manual, Catalog 5145, published 2010, retrieved the internet on Dec. 12, 2015 from <http://www.yumpu.com/en/document/view/30138118/exomirtm-kit-manual-nordic-biosite/>.*

Hubert Rehm, Binding Assays with Membranes, Jan. 1, 2006, chapter 2.2 Binding, Protein Biochemistry and Proteomics, Elesevier, pp. 37-39.*

International Search Report and Written Opinion from PCT/US2011/040015, Mailed, Jan. 5, 2012.

Jimenez et al., Endothelial microparticles released in thrombotic thrombocytopenic purpura express von Willebrand factor and markers of endothelial activation., Br. J. Hematol., vol. 123(5): 896-902 (2003).

Labsource. Whatman Glass Microfiber Filters, 2009. [Retreived from the Internet Dec. 12, 2011; ,URL://http://www.labsource.com/Catalog/Group.aspx?GroupID=82>].

Miranda et al., Nucleic acids within urinary exosomes/microvesicles are potential biomarkers for renal disease., Kidney Intl., vol. 78(2):191-199 (Apr. 28, 2010).

Chen et al., Lab Chip 2010, vol. 10, pp. 505-511.

Hotfilder et al., British Journal of Haematology, 1999, vol. 106, pp. 335-344.

Ito et al., Bone Marrow Transplantation, 2003, vol. 32, pp. 391-398.

Haas et al., Blood, vol. 83, No. 12, Jun. 15, 1994, pp. 3787-3793.

Gene Cards DEFA3 Gene, first internet archive Aug. 7, 2010, p. 1-14.

Cutillas et al., The urinary proteome in Fanconi syndrome implies specificity in the reabsorption of proteins by renal proximal tubule cells., Am. J. Physiol. Renal Physiol., vol. 287(3):F353-364 (2004).

Hashem, Biochemical and expression studies on Acquaporin 9 (AQP9) in wild and AQP9 knockout mice, Veterinarski Archie, vol. 80(1):93-112 (2010).

Hewitt et al., Discovery of Protein Biomarkers for Renal Diseases, J. Am. Soc. Nephrol., vol. 15(7): 1677-1689 (2004).

International Search Report and Written Opinion for PCT/US2011/040057, mailed Oct. 21, 2011.

Miranda et al., Nucleic acids within urinary exosomes/microvesicles are potential biomarkers for renal disease, Kidney International, vol. 78(2): 191-199 (Apr. 28, 2010).

(56) References Cited

OTHER PUBLICATIONS

Zefon International. Glass Fiber Filters, Jan. 14, 2010 [retreived from the internet Oct. 7, 2011; <http://web.archive.org/web/20100114112921/http://www.zefon.com/store/glass-fiber-filters/>].

Zhou et al., Urinary exosomal transcription factors, a new class of biomarkers for renal disease, Kidney International, vol. 74(5):613-621 (2008).

International Preliminary Report on Patentability, re PCT Application No. PCT/US2011/40015, mailed Dec. 27, 2012.

Japanese Notice of Reason for Rejection, re JP Application No. 2013-514399, mailed Aug. 19, 2014.

Barnett et al., Angiotensin-Receptor Blockade versus Converting-Enzyme Inhibition in Type 2 Diabetes and Nephropathy, N Eng J Med (2004) 351:1952-61.

Erusalimsky et al.: A Glass Fiber/Diethylaminoethyl Double Filter Binding Assay That Measures Apoptotic Internucleosomal DNA Fragmentation, Analytical Biochemistry 242, 187-196 (1996) Article No. 0452.

Ferguson et al.: Vesicular Localization and Activity-Dependent Trafficking of Presynaptic Choline Transponders, The Journal of Neuroscience, Oct. 29, 2003, 23(30):9697-9699.

Klein et al., Ex-Vivo Assessment of Candidate Anti-Inflammatory Agents in the Treatment of Gram Negative Sepsis, Immun & Infec Dis (1994) vol. 4(1):33-35.

Lescuyer et al., Proteomics: Clinical Applications (2008) vol. 2(7-8):1008.

Murakami et al.: "Development of Glomerulus-, Tubuel-, and Collecting Duct-Specific mRNA Assay in Human Urinary Exosomes and Microvesicles," PLOS ONE vol. 9, Oct. 2014, pp. 1-10.

Notterman et al., in Microarrays and Cancer Research (2002) Warrington et al. (eds.) pp. 81-111 at pp. 81-82.

Strausberg et al., Reading the Molecular Signatures of Cancer, Microarrays & Cancer Res (2002) pp. xi-xvi.

Tomblyn et al., Guidelines for preventing infectious complications among hematopoietic cell transplantation recipients: A global prespective, Biol Blood Marrow Trans (2009) vol. 15:1143-1238.

Wellmann et al., Detection of differentially expressed genes in lymphomas using cDNA arrays: identification of clusterin as a new diagnostic marker for anaplastic large-cell lymphomas, Blood (2000) vol. 96(2):398-404.

Zheng et al., Urinary Podocyte-Associated mRNA profile in Various Stages of Diabetic Nephropathy, PLOS one (2011) vol. 6(5):1-7.

Zucker et al., Immature platelet fraction as a predictor of platelet recovery following hematopoietic progenitor cell transplantation, Lab Hematol (2006) vol. 12:125-130.

* cited by examiner

Figure 2G
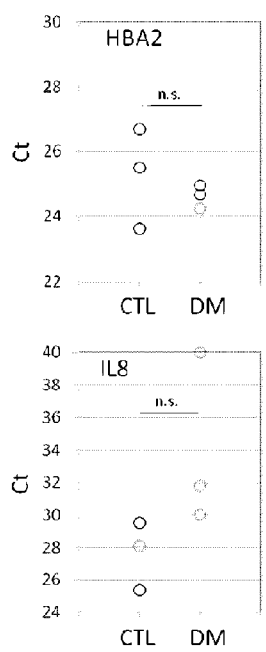
Figure 2H
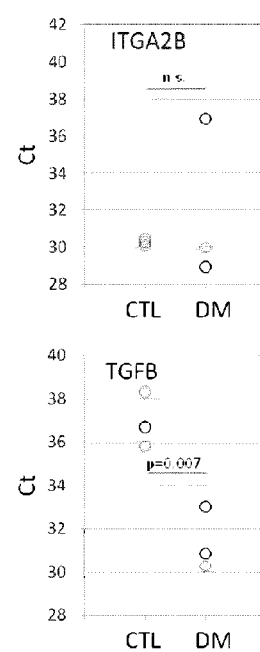
Figure 2I
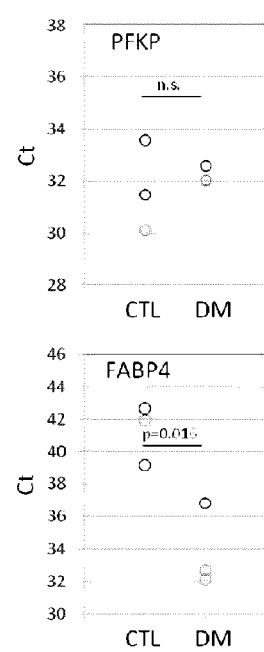
Figure 2J
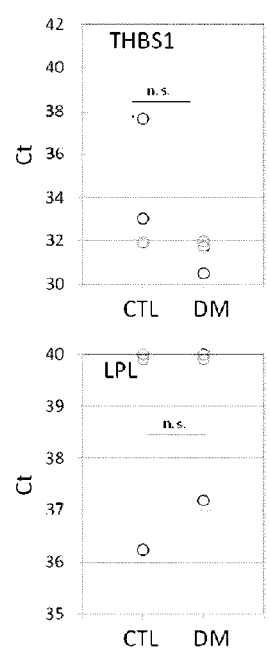
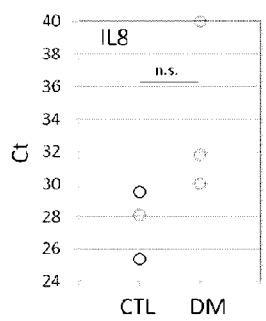
Figure 2K
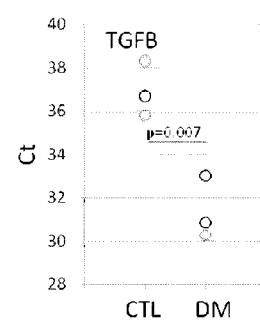
Figure 2L
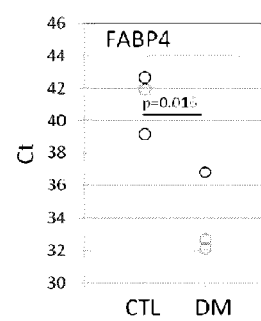
Figure 2M
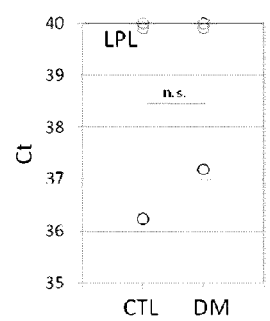
Figure 2N

METHOD OF CHARACTERIZING VASCULAR DISEASES

RELATED CASES

The contents of each priority document listed in the associated Application Data Sheet is incorporated in its entirety by reference herein. This application also incorporates by reference the sequence listing submitted as ASCII text filed concurrently via EFS-Web. The Sequence Listing is provided as a file entitled "ST25 Sequence Listing—HITACHI.101P1", created on Dec. 10, 2012 and which is 12.0 kilobytes in size.

BACKGROUND OF THE INVENTION

1. Field of the Invention

The present disclosure relates to diagnosis of disease and measurement of homeostatic status from a sample of whole blood. More specifically, the present disclosure relates to the field of characterizing RNA that is contained in vesicles from whole blood to diagnose disease.

2. Description of Related Art

In many cases, physicians interpret a patient's symptoms, medical history and the results of a physical exam to derive an initial diagnosis. Medical tests are an integral part of confirming or modifying an initial diagnosis. Such tests may include a range of different tests, from simple, non-invasive tests such as blood pressure measurements, monitoring the patient's temperature, medical imaging (e.g., x-rays), to minimally invasive tests such as, for example, blood tests, to more invasive tissue biopsies and even in-patient surgical biopsies. Much of the decision tree that directs which tests are performed are based on the clarity of the symptoms experienced by the patient, the physical exam, and the information gained by non- or minimally-invasive diagnostic tests. However, some diseases are difficult to diagnose, possibly because of vague, inconsistent, or overly common symptoms and therefore require a more invasive and/or directed diagnostic approach.

Currently, some diagnostic medical tests are performed on blood extracted from a patient to diagnose a disease from a biochemical pattern that is not present in healthy patients or is altered from a previously obtained patient sample. These tests commonly utilize plasma or serum and measure, for example electrolytes, urea, creatinine, and glucose, among other analytes. Other tests measure plasma proteins such as albumins, immunoglobulins, fibrinogens, and regulatory proteins. Some tests measure other biological compounds, such as, for example, thiamin, riboflavin, niacin, vitamin B6, folic acid, vitamin D, biotin, iron, and clotting factors factor V and factor X.

However, these diagnostic tests are typically based upon the presence of known and well characterized markers in the blood. For instance, diagnostic tests for HIV infection detect antibodies in the blood of a patient. However, there is a window soon after infection where the immune system has not yet generated antibodies and the levels of disease-associated marker proteins are minimal, making detection difficult. In some circumstances, the use of an antibody based test, such as an ELISA or a western blot, may not be feasible because it may not be possible to generate antibodies with adequate affinity or avidity for their target protein. The target antigen or protein may also change conformation or be unstable when taken out of the body. Moreover, antibodies may bind to other (non-target) proteins non-specifically. Additionally, certain diagnostic tests employ chemical reactions (e.g., colorimetric changes) to identify markers from blood or other fluid samples. Such tests may also be affected by similar limitations as are described above (e.g., reliance on known reactants, sensitivity, etc.). Thus, there exists a need for a sensitive, accurate and reproducible diagnostic test for a variety of diseases that allows for early detection and/or diagnosis of a disease.

SUMMARY

In several embodiments, there is provided a method for enabling a medical professional to recommend a disease-specific and disease status-specific therapy to a patient comprising, the method comprising obtaining a first sample of a biological fluid from the patient, wherein the sample comprises vesicles that are associated with RNA, capturing the vesicles from the sample, lysing the vesicles to release the vesicle-associated RNA, wherein the vesicle-associated RNA comprises an RNA associated with the disease and an RNA associated with a specific tissue, quantifying the disease-specific and tissue-specific RNAs, comparing the quantity of the disease-specific RNA and the tissue-specific RNA to the quantity of corresponding RNAs from subjects without the disease, wherein a difference between the quantity of the disease-specific RNA from the patient as compared to the non-diseased subjects indicates a diseased state, and wherein the type of disease affecting the patient is identified by the tissue-specific identity of the tissue-specific RNA; and 1) indicating to a medical professional the type of disease affecting the patient and 2) indicating to the medical professional the state of the disease, thereby enabling the medical professional to recommend a disease-specific and disease status-specific therapy to the patient.

In several embodiments, there is provided a method for advising a subject to undertake a disease-specific and disease status-specific therapy comprising, ordering a test of a biological fluid from the subject, the test comprising obtaining a first sample of a biological fluid from the patient, wherein the sample comprises vesicles that are associated with RNA, capturing the vesicles from the sample, lysing the vesicles to release the vesicle-associated RNA, wherein the vesicle-associated RNA comprises an RNA associated with the disease and an RNA associated with a specific tissue, quantifying the disease-specific and tissue-specific RNAs, comparing the quantity of the disease-specific RNA and the tissue-specific RNA to the quantity of corresponding RNAs from subjects without the disease, wherein a difference between the quantity of the disease-specific RNA from the patient as compared to the non-diseased subjects indicates a diseased state, and wherein the type of disease affecting the patient is identified by the tissue-specific identity of the tissue-specific RNA; and advising the subject to undertake a specific therapy based on the type of disease and the state of the disease.

In several embodiments, the biological fluid comprises whole blood, blood plasma, cerebrospinal fluid. Other biological fluids are used in other embodiments. In some embodiments, the biological fluid comprises whole blood and the method further comprises removing erythrocytes and cellular blood components from the whole blood.

In several embodiments, the quantification method is selected from the group consisting of reverse-transcription polymerase chain reaction (RT-PCR), real-time RT-PCR, northern blotting, fluorescence activated cell sorting, ELISA, and mass spectrometry.

In several embodiments, there is provided a method for determining the type of disease affecting a patient and disease status of a patient, the method comprising obtaining a first sample of a biological fluid comprising vesicles associated with RNA from the patient, capturing the vesicles from the sample, lysing the vesicles to release the vesicle-associated RNA, the vesicle-associated RNA comprising an RNA associated with the disease and an RNA associated with a specific tissue, quantifying the disease-specific and tissue-specific RNAs, and determining the disease status of the patient by comparing the quantity of the disease-specific RNA and the tissue-specific RNA to the quantity of corresponding RNAs from subjects without the disease, wherein a difference between the quantity of the disease-specific RNA from the patient as compared to the non-diseased subjects indicates a diseased state, and wherein the type of disease affecting the patient is identified by the tissue-specific identity of the tissue-specific RNA.

In several embodiments, there is also provided a method of monitoring the ongoing health of a patient comprising determining the type of disease affecting a patient and the disease status of the patient according to the method above, obtaining a second sample of biological fluid from the patient at a later time as compared to the first sample, wherein the second sample comprises vesicles that are associated with RNA, capturing the vesicles from the second sample, lysing the vesicles to release the vesicle-associated RNA, wherein the vesicle-associated RNA comprises an RNA associated with the disease; and quantifying the disease-specific RNAs, wherein a difference in the quantity of the disease-specific RNA is between the first sample and the second sample is correlated with a progression or regression of the disease. In one embodiment, a therapy is administered between obtaining the first and the second samples. In several embodiments, the method, further comprises obtaining a plurality of additional samples over time and monitoring the disease status of the patient over time.

In several embodiments, the capturing comprises filtering the sample through one or more filter membranes, wherein the vesicles associated with RNA are captured on the one or more filter membranes. In several embodiments, the vesicles are isolated by a method comprising loading at least a portion of the first sample of fluid into a sample loading region of a vesicle capture device, passing the fluid from the sample loading region through a vesicle-capture material in the vesicle capture device, the vesicle-capture material comprising glass-like materials to produce a supernatant, passing the supernatant to a sample receiving region of the vesicle capture device and discarding the supernatant, wherein the passings result in capture of the vesicles from the fluid sample on or in the vesicle-capture material, thereby capturing the vesicles. In some embodiments, the vesicle-capture material comprises a plurality of layers of the material. In several embodiments the plurality of layers of the vesicle-capture material comprises at least a first layer and a second layer of glassfiber. In several embodiments, the biological fluid is passed through the first layer of glassfiber so as to capture material from the biological sample that is about 1.6 microns or greater in diameter. In several embodiments, the biological fluid is passed through the second layer of glassfiber so as to capture vesicles having a minimum size from about 0.6 microns to about 0.8 microns in diameter, and having a maximum size of less than 1.6 microns.

In some embodiments, the method further comprises eluting the vesicle-associated RNA released after the lysis to isolate extracellular RNA.

In several embodiments, the vesicle-associated RNA released by the lysis is mRNA. In some embodiments, the method further comprises hybridizing the mRNA to oligo-dT, synthesizing cDNA, and quantifying disease-specific and tissue-specific mRNA by PCR amplification employing using primers directed to disease-specific markers and primers directed to tissue-specific markers.

In several embodiments, the disease-specific and the tissue-specific RNAs are the same. However, in other embodiments, the disease-specific and the tissue-specific RNAs are different RNAs. In some embodiments, the disease-specific and the tissue-specific RNAs are the same type of RNA, while in other embodiments they are different types of RNA.

In some embodiments, the biological fluid comprises whole blood. In one embodiment, the method further comprises removing erythrocytes and cellular blood components from the whole blood.

In some embodiments, the biological fluid comprises blood plasma.

In some embodiments, biological fluid comprises cerebrospinal fluid.

In some embodiments, the tissue-specific RNA is derived from endothelial cells. In some embodiments, the disease-specific RNA is derived from endothelial cells. In some embodiments, the tissue-specific RNA and the disease-specific RNA are derived from endothelial cells.

In some embodiments, the tissue-specific RNA is derived from atherosclerotic plaques. In some embodiments, the disease-specific RNA is derived from atherosclerotic plaques. In some embodiments, the tissue-specific RNA and the disease-specific RNA are derived from atherosclerotic plaques.

In some embodiments, the tissue-specific RNA is derived from adipose tissue. In some embodiments, the disease-specific RNA is derived from adipose tissue. In some embodiments, the tissue-specific RNA and the disease-specific RNA are derived from adipose tissue.

In some embodiments, the tissue-specific RNA is selected from the group consisting of: mRNA, viral RNA, microRNA, snRNA, and poly(A)+ RNA). In some embodiments, the disease-specific RNA selected from the group consisting of: mRNA, viral RNA, microRNA, snRNA, and poly(A)+ RNA).

In several embodiments, the disease and tissue-specific RNA encodes von Willebrand Factor and the type of disease is a vascular disease. In several embodiments, the vascular disease is selected from the group consisting of: atherosclerosis, hypertension, cardiovascular diseases, obesity, hypercholesterolemia, diabetes, and collagen diseases.

In several embodiments, the type of disease is obesity and the disease and tissue-specific RNA is selected from the group consisting of: adipose tissue marker adiponectin (ADIPOQ), leptin, ghrelin, thyroid hormone T3, thyroid hormone T4, glucagon-like peptide-1 (GLP-1), and insulin. In one embodiment, the disease and tissue-specific RNA is ADIPOQ.

In several embodiments, the type of disease is a lung disease and wherein the disease and tissue-specific RNA is selected from the group consisting of: angiotensin I converting enzyme (ACE), surfactant protein A, surfactant protein B, surfactant protein C, surfactant protein D, and mucin.

In several embodiments, the type of disease is a bone disease and wherein the disease and tissue-specific RNA is selected from the group consisting of: osteoblast marker periostin (POSTN), type-1 collagen, osterix, collagen-1, bone sialoprotein, macrophage colony-stimulating factor, and alkaline phosphatase.

There is also provided herein a method of isolating extracellular RNA from plasma comprising obtaining a plasma sample comprising extracellular vesicles associated with RNA, filtering the plasma samples through one or more filter membranes, wherein the vesicles associated with RNA are captured on the one or more filter membranes, lysing the captured vesicles with a lysis buffer to dissociate the RNA, and eluting the dissociated RNA, thereby isolating extracellular RNA.

In several embodiments, the RNA is selected from the group consisting of: mRNA, viral RNA, microRNA, snRNA, and poly(A)+ RNA).

There is also provided herein a method of quantifying extracellular RNA from plasma comprising capturing extracellular RNA-containing vesicles from a plasma sample on one or more membranes, lysing the vesicles with a lysis buffer to yield a lysate comprising RNA on the one or more membranes, transferring lysate to oligo(dT)-immobilized solid support, and quantifying the amount of the RNA from the sample.

In several embodiments, the RNA is selected from the group consisting of: mRNA, viral RNA, microRNA, snRNA, and poly(A)+ RNA). In one embodiment, the RNA is quantified by RT-PCR.

There is additionally provided herein a method of monitoring the ongoing health of patient comprising obtaining a first sample of whole blood from the patient, wherein the first sample comprises vesicles that are associated with a first RNA, lysing the vesicles to release the first vesicle-associated RNA, wherein the first vesicle-associated RNA comprises an RNA associated with the disease and with a specific tissue, quantifying the disease and tissue-specific RNA, and obtaining a second sample of whole blood from the patient, wherein the second sample is isolated at a later time as compared to the first sample, wherein the second sample comprises vesicles that are associated with second RNA lysing the vesicles to release the second vesicle-associated RNA wherein the second vesicle-associated RNA is associated with the same disease and tissue as the first vesicle-associated RNA, and quantifying the first and second RNAs, wherein a difference in the quantity of the first and second RNAs is correlated with a progression or regression of the disease.

In several embodiments, a therapy is administered between obtaining the first and the second samples. In several embodiments, the RNA comprises one or more markers of inflammation, wherein the markers are selected from the group consisting of IL-5, IL-8, IL-13, RANTES, MIP-α, and eotaxin. In one embodiment, the RNA comprises RNA of fetal origin. In some embodiments, the RNA comprises one or more markers of cell type, wherein the markers are selected from the group consisting of angiotensin (AGT), preprosinsulin, myostatin (MSTN), Renin, CD14, and CD3. In several embodiments, the RNA is selected from the group consisting of SARS-associated coronavirus, influenza, hepatitis C, influenza A, HIV, foot-and-mouth disease virus, Human bocavirus (HBoV) and *Trypanosoma brucei*. In one embodiment, the patient is a pregnant mammal and wherein the vesicles are of fetal origin. In one embodiment, the patient is a fetus. In several embodiments, the markers of fetal origin are selected from the group consisting of placenta-specific 1 (PLAC1), placenta-specific 4 (PLAC4), Chorion-specific transcription factor GCM1, ZDHHC1, pregnancy-associated plasma protein A (PAPPA), pregnancy-specific beta-1-glycoprotein 9 (PSG9), tissue factor pathway inhibitor 2 (TFPI2), and metastasis suppressor gene KISS1. In several embodiments, the RNA comprises one or more markers associated with cholesterol metabolism, wherein the markers are ATP-binding cassette (ABC) transporter ABCA GCN20, ATP-binding cassette (ABC) transporter ABCA white, the ATP-binding cassette transporter, sub-family A, member 1 (ABCA1) and cholesterol efflux regulatory protein (CERP).

In several embodiments, the RNA comprises one or more markers of blood homoestasis, wherein the markers are selected from the group consisting of Willebrand factor (vWF), thrombin, factor VIII, plasmin, and fibrin. In several embodiments, the RNA comprises one or more markers of basal cellular function, wherein the markers are selected from the group consisting of transcription factor glyceraldehyde 3-phosphate dehydrogenase, succinate dehydrogenase subunit A, NADH dehydrogenase [ubiquinone] 1 alpha subcomplex subunit 1, β actin, β2 microglobulin, and heat shock protein 90. In several embodiments, the RNA comprises one or more markers of kidney cell origin, wherein the markers are selected from the group consisting of Tamm-Horsfall glycoprotein (THP), angiotensinogenase, angiotensin I converting enzyme, preproinsulin, glucagon, insulin, amylin, and ghrelin. In several embodiments, the RNA comprises one or more markers of cancer, wherein the markers are selected from the group consisting of carcino-embryonic antigen (CEA), mucin, alpha-fetoprotein, tyrosinase, melanoma associated antigen, tumor protein 53, prostate-specific antigen (PSA) and thyroglobulin. In several embodiments, the specific RNA comprises one or more markers of immune system function, wherein the markers are selected from the group consisting of CD16, granzyme B, and TNF-alpha, CD25, forkhead box P3 (FoxP3), and cytotoxic T-lymphocyte antigen-4 (CTLA4). In several embodiments, the RNA comprises one or more markers of adhesion mediated cardiovascular disease, wherein the markers are selected from the group consisting of selectin (SELE), E-selectin, L-selectin, P-selectin, and vascular endothelial marker cadherin 5 (CDH5). In several embodiments, the RNA comprises one or more markers of stem cell type, wherein the markers are selected from the group consisting of fetal liver kinase-1 (Flk1), smooth muscle cell-specific myosin heavy chain, vascular endothelial cell cadherin, alkaline phosphatase, hydroxyapatite, osteocalcin, bone morphogenetic protein receptor, and stem cell marker prominin 1 (PROM1, CD133).

In several embodiments, the vesicle-associated RNA comprises one or more markers of cancer, wherein the markers are selected from the group consisting of KRTs, MMPs, WT1, and mucin.

In several embodiments, the RNA is hybridized to oligo-(dT).

There is also provided herein a method for determining disease status of a patient, the method comprising obtaining a sample of whole blood from the patient, wherein the sample comprises vesicles that are associated with RNA, concentrating the vesicles from the sample, lysing the vesicles to release the vesicle-associated RNA, wherein the vesicle-associated RNA comprises RNA associated with the disease, quantifying the RNA from the vesicles; and determining disease status of the patient by comparing the quantity of the RNA to corresponding RNA from patients without the disease.

There is also provided herein a method for diagnosing a disease comprising concentrating RNA-associated vesicles from the cerebrospinal fluid of a patient, quantifying RNA specific to cerebrospinal-associated diseases from the vesicles; and determining disease status of the patient by comparing the quantity of specific RNA to a control.

There is also provided herein a method for diagnosing a disease comprising collecting whole blood from a patient, removing erythrocytes and cellular blood components, concentrating vesicles by filtration on a filter membrane, lysing the vesicles on the filter membrane to produce lysate that contains mRNA, hybridizing the mRNA to oligo-dT, synthesizing cDNA, quantifying specific mRNA by PCR amplification employing using primers directed to disease markers and primers directed to control markers, and determining disease status by comparing the level of specific mRNA associated with disease markers with specific RNAs associated with a control.

There is also provided herein a method of monitoring patient health comprising collecting blood from a patient at a first time point and quantifying specific RNA from vesicles, collecting blood from the patient subsequent to the first time point and quantifying specific RNA from the vesicles, wherein changes in RNA expression between the time points reflects changes in the disease state of the patient. In several embodiments, medication is administered to the patient subsequent to time zero.

There is additionally provided method for determining disease status and tissues affected by a disease, the method comprising obtaining a sample of whole blood from a patient, wherein the sample comprises vesicles that are associated with RNA, concentrating the vesicles from the sample, lysing the vesicles to release the vesicle-associated RNA, wherein the vesicle-associated RNA comprises a first RNA associated with the disease, wherein the vesicle-associated RNA comprises a second RNA associated with a tissue affected by the disease, quantifying the first RNA and the second RNA, determining disease status of the patient by comparing the quantity of the first RNA to corresponding RNA from patients without the disease; and determining tissue affected by the disease by identifying the tissue associated with the second RNA.

DETAILED DESCRIPTION

General

Figure 1:
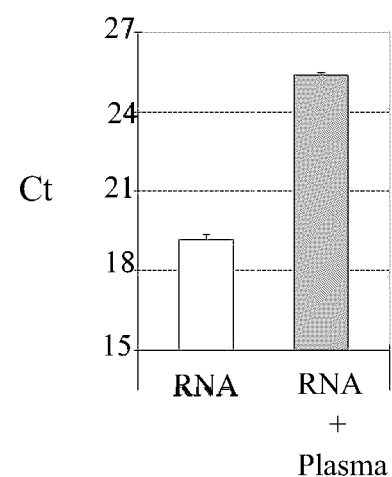
FIG. 1 depicts measurement of naked RNA in plasma.

A physician's diagnosis is typically based upon the medical history of the patient as well as current symptoms. In addition to a physical examination that may expose signs of the underlying disease, diagnostic tests may be ordered to confirm an initial diagnosis. Several embodiments of the methods described herein are applicable to a wide range of disease states as well as to patients with healthy (normal) homeostasis.

Diagnostic techniques based on nucleic acid detection offer an alternative to protein detection that, in many cases, provides a higher degree of sensitivity. For example, HIV viral load can be assessed by PCR using naked RNA from the plasma of a patient, in some instances viral load as low as 40 HIV copies/mL can be attained. However, as discussed below, naked RNA is rapidly degraded in plasma. Thus, there is a limitation to even the most sensitive PCR-based assays when using highly labile naked RNA. Additionally, mRNA concentrations in plasma are typically low, thereby requiring large volumes of blood as a starting material. In some contexts, the high volume makes sample manipulation difficult.

Diagnosis of certain types of diseases is particularly hindered by the limitations of current diagnostic tests and assays. For example, many diseases that are progressive in nature may not display markers that can be detected by traditional diagnostic methods until the disease is well-established. In such cases, as the disease progresses, the prognosis becomes increasingly poor. As such, early detection of the disease may lead to easier treatment regimes and possibly a significantly improved patient outcome. For example, cardiovascular disease, a leading cause of preventable death, may not be diagnosed until a patient exhibits severe symptoms, such as a myocardial infarction or stroke. Moreover, many cardiovascular diseases are associated with obesity or other disease states that may mask the symptoms of the underlying cardiovascular disease.

Thus, there exists a need for a sensitive diagnostic test that does not rely on the use of highly labile naked RNA or require large volumes of blood to be collected from a patient. Moreover, there is a need for a more sensitive alternative to the diagnostic tests currently used in the detection and characterization at early stages of diseases (e.g., atherosclerosis, hypertension, cardiovascular diseases, obesity, hypercholesterolemia, diabetes, collagen diseases, cancers, etc.).

Vesicle-Associated RNA

In some embodiments disclosed herein, there are provided methods for the capture of RNA from a patient blood sample and subsequent analysis of that RNA for disease and/or tissue specific markers. In several embodiments, the method comprises isolated of vesicles associated with RNA from the blood sample. As a result, a small sample of whole blood may be obtained from a patient and be used in a rapid and sensitive diagnostic assay that can detect low circulating levels of nucleic acids associated with a disease (e.g., a blood borne disease marker or an infectious organism) or tissue-associated nucleic acids that are not normally present in the blood. In some embodiments, a tissue/disease specific marker not normally present in the blood is quantified, with increased levels in the blood being indicative of disease. In other embodiments, detection of a reduced level of a tissue/disease specific marker is indicative of a disease. In some embodiments, disease specific markers are analyzed from a sample, which is further analyzed to identify tissue specific markers, allowing for a determination of what tissue is affected by a particular disease. Several embodiments of the methods disclosed herein are advantageous because they do not require large volumes of blood to be drawn and/or utilize vesicle associated RNA, which is more resistant to degradation than free RNA in the blood. While the assay of blood associated vesicles is in several embodiments disclosed herein, it will be appreciated by one of skill in the art that other body fluids can serve as a source of vesicles. Vesicles may be obtained from plasma, serum, urine, cerebrospinal fluid, sputum, saliva, mucus, tears etc.

Several embodiments quantify RNA which may be indicative of a disease state and is therefore used to determine a patient's disease status. According to various embodiments, various methods to quantify mRNA are used, including Northern blot analysis, RNAse protection assay, PCR, nucleic acid sequence-based amplification, branched-DNA amplification, and DNA or RNA microarray analysis. Additionally, in some embodiments, vesicle associated RNA may be analyzed using Chip-Sequencing, which combines chromatin immunoprecipitation with nucleic acid sequencing to identify protein-nucleic acid interactions. In several embodiments, RNA is used as a template for screening expression of disease associated genes (for example, over time or as compared to a control) and/or is screened for markers correlated to tissue or cell type. As such, not only can a patient's disease status be evaluated from a peripheral blood sample, but information regarding which tissue is diseased is also obtained. In some embodiments, a single marker is used to indicate both a disease state and the tissue affected. For example, a marker that is specific for a tissue and is not present (or present at a certain level) in the blood under normal physiologic conditions that is detected in the blood at an altered level (compared to normal conditions) provides simultaneous information regarding disease state and the tissue affected. Thus, several embodiments of the methods comprise a sensitive non-invasive technique to determine the type of disease state or cellular injury suffered by the patient and, if desired, the organ or location of the damage.

In several embodiments, diagnosis and characterization of disease are performed by detection and quantification of specific RNA species from RNA-containing vesicles isolated from blood samples. In some embodiments, such vesicles from whole blood are trapped on a filter, thereby allowing RNA extraction from the vesicles. In some embodiments, the vesicles comprise a tissue-specific marker, which allows the vesicles to be traced back to their organ or tissue of origin. Thus, in some embodiments, markers of diseases that typically afflict internal organs are evaluated via collection of a peripheral sample of blood.

RNAses, which degrade RNA, are known to be elevated in some disease states, for example, in certain cancers. The extracellular environment, including the plasma or serum, is known to contain substantial quantities of RNAses. Given this context, extracellular RNA is often considered a meaningless degradation product in the blood, not only because its levels may not be representative of the true levels of the intracellular message, but also due to the instability and poor quality of the RNA. Amplifiable extracellular DNA from some tumors has been found in plasma and serum but RNA is also much less stable in the blood than freshly isolated intracellular DNA. Cellular tyrosinase mRNA has been amplified in order to detect circulating malignant melanoma cells. However, the detection of circulating cells is correlated with late stage disease or a high tumor burden, both of which are associated with a negative patient prognosis. Other disease modalities, such as cardiovascular diseases, would benefit from early detection of the damage, inflammation, and structural defects in blood vessels that may be associated with, for example, atherosclerosis, degenerative diseases, dysplastic disorders, vascular inflammation and thrombosis, and thromboembolism. Several embodiments provide a more sensitive method of detecting both localized disease and low concentrations of disease-associated markers.

Due to the rapid rate of RNA degradation in the extracellular environment, conventional understanding suggests that many organs and tissues are unable to provide blood-borne RNA suitable as a diagnostic target, because RNA would be degraded in the bloodstream well before it could be used as a template for detection. However, Applicant has unexpectedly discovered that extracellular RNA, when evaluated according to several of the methods disclosed herein, advantageously allows for the detection of disease specific markers and/or tissue specific markers, from a sample of peripheral blood.

In many studies attempting to detect extracellular RNA in plasma, serum is filtered through a small pore size filter, which removes intact cells, or by low speed centrifugation. These methodologies fail to recognize that a valuable proportion of extracellular RNA is vesicle associated. Extracellular RNA is associated with one or more of membrane particles (ranging in size from 50-80 nm), exosomes (ranging in size from 50-100 nm), exosome-like vesicles (ranging in size from 20-50 nm), and microvesicles (ranging in size from 100-1000 nm). In several embodiments these vesicles are isolated and/or concentrated, thereby preserving vesicle associated RNA despite the high RNAse extracellular environment. In several embodiments, these techniques utilized this unexpected source of high quality RNA to increase the sensitivity of diagnostic methods. Even after the recognition that some RNA is vesicle associated, many RNA purification techniques have not been adapted to efficiently capture and preserve vesicle associated RNA. Typically, whole blood components are separated by diluting the blood with an isotonic solution followed by density centrifugation. The non-cellular plasma fraction is then subjected to high speed centrifugation to cause vesicle sedimentation or pelleting. This approach is time consuming and requires expensive and specialized equipment as compared to the format used in several embodiments. Moreover, in some cases, RNA may be damaged by the high pressures that accompanying ultra-centrifugation. In some embodiments, the methods described herein are fast, inexpensive, highly reproducible, and have low variability between replicated measurements. Moreover, several embodiments therefore are particularly advantageous in that they do not require lengthy protocols that risk RNA degradation.

In several embodiments, the methods and apparatus described herein use different types of filters to capture vesicles of different sizes. In some embodiments, differential capture of vesicles is made based on the surface expression of protein markers. By having a filter that is reactive to a specific surface marker, such as a filter coupled to an antibody that binds a marker on the surface of the vesicle, specific types of vesicles or vesicles of different origins are isolated. The markers may be protein or peptides which may additionally be modified by addition of, for example, lipids, carbohydrates, and other molecules such as acylated, formylated, lipoylated, myristolylated, palmitoylated, alkylated, methylated, isoprenylated, prenylated, amidated, glycosylated, hydroxylated, iodinated, adenylated, phosphorylated, sulfated, and selenoylated, ubiquitinated. The vesicle markers may also be, but are not limited to, non-proteins such as lipids, carbohydrates, nucleic acids, RNA, DNA, etc. Such specialized purification of vesicles, and their associated RNA, is not achievable with mere analysis of unaltered plasma or centrifuged plasma.

In some embodiments, vesicles from different organs or tissues are specifically identified, fractionated into different samples, and analyzed separately. In several embodiments, this approach captures cell markers based on expression of, for example, CD66b-neutrophil, CD202b-endothelial, CD206-macrophage/dendritic, CD79a-B-cell, CD14-monocyte, CD41a-platelet, CCR3-dendritic cell, CCR5-monocyte, or CD3-T-cell markers on the surface of vesicles.

In several embodiments, the specific capture of vesicles based on their surface markers also enables a "dip stick" format where each different type of vesicle is captured by dipping probes coated with different capture molecules such as antibodies with different specificities into a blood sample. For example, probes with antibodies reactive to vascular endothelial, liver, lung (or other) markers can be immersed into a sample of whole blood to capture the different types of vesicles. In some embodiments, an invasive probe accommodating several different specificities can be inserted into a vein or artery and directly sample the bloodstream. This real time sampling serves to concentrate vesicles from a large volume of blood without actually removing a large quantity of blood from the patient.

Such real time monitoring is also compatible with surgical techniques where the blood is circulated as part of the operative procedure such as coronary artery bypass surgery. In several embodiments, patient blood is monitored during a procedure (e.g., surgery), and vesicle capture is used to detect stresses placed on any organ by including a specific organ capture as part of the probe.

Disease Applications and Cellular Markers

Several embodiments described herein are advantageous because vascular endothelial markers associated with vascular diseases can be rapidly assessed in a high through put protocol. Such an in vivo sampling approach is impossible with traditional sampling techniques that require ultracentrifugation or other specialized and/or extensive isolation procedures. Several embodiments are used to diagnose or monitor vascular diseases including, but not limited to, atherosclerosis, hypertension, cardiovascular diseases, obesity, hypercholesterolemia, diabetes, and collagen diseases. The main pathological site involved with vascular disease is the blood vessel endothelium, which is the inner layer of blood vessels. Thus, the endothelial cell-specific mRNA is a target for diagnosis in some embodiments. As discussed above, in several embodiments a marker that is tissue specific and present in the blood at a given level in a non-diseased state, when detected at an altered level in the blood, provides information regarding both the tissue affected and the disease status of the subject. In some embodiments, a disease specific marker and a second tissue specific marker are evaluated independently from a sample to characterize disease status and tissue identity.

Atherosclerosis (arteriosclerotic vascular disease) results from the build up of fatty materials such as cholesterol in the arteries resulting in a thickening of the arterial wall. Commonly referred to as "hardening of the arteries," this condition is characterized by the formation of multiple plaques in the arteries. The disease may progress asymptomatically until plaque rupture which can lead to permanent debilitation or sudden death. Severe narrowing of the arteries can be detected by angiography and stress testing although these methods do not detect the underlying atherosclerosis disease. However, it is more difficult to detect minor narrowing of the arteries at early stages in the disease, at time at which diagnosis could lead to lifestyle changes and/or medication that would prevent the more serious effects later in the disease. Thus, there is need of a method for early diagnosis of disease prior to onset of symptoms.

Several embodiments detect markers of atherosclerotic disease associated with obesity such as, for example, adipose tissue marker adiponectin (ADIPOQ), leptin, pro-opiomelanocortin, neuropeptide Y, agouti-related protein, orexin A and B, ghrelin, thyroid hormones including T3 and T4, peptide YY (peptide tyrosin tyrosin), glucagon-like peptide-1 (GLP-1), oxyntomodulin, cholecystokinin, and insulin.

Leptin is a peptide hormone produced by fat cells that regulates appetite and fat storage. Increased levels of leptin can cause long-term cardiovascular damage similar to hypertension, arthrosclerosis, and diabetes. In some embodiments, vesicle-associated RNA is obtained from a patient and levels of leptin mRNA are quantified. The level of leptin mRNA is compared to healthy individuals or a control level so that obesity and/or cardiovascular damage can be diagnosed.

Hypertension or high blood pressure is a persistent or intermittent elevation of systolic, diastolic pressure, or both. Hypertension is a risk factor for heart attacks, heart failure, strokes, arterial aneurysm, and chronic kidney failure. Elevation of arterial blood pressure also reduces life expectancy. Most patients with primary hypertension are asymptomatic until complications have occurred. Therefore, there is a need for a test that can lead to early diagnosis of the condition. The method described herein can be applied to the detection of markers, such as inflammatory markers, high-sensitivity C-reactive protein (hsCRP), and soluble (s) E-selectin (among others) that may be associated with the degenerative effects of hypertension.

Hypercholesterolemia is characterized by high levels of cholesterol in the blood. Hypercholesterolemia may be a secondary consequence of other diseases such as cardiovascular disease. Hypercholesterolemia is also related to hyperlipoproteinemia in which there are elevated levels of lipids in the blood. Lipoproteins transport triglycerides and cholesterol in the plasma and an elevated level of these components may cause or worsen preexisting atherosclerosis. In some embodiments, markers associated with cholesterol metabolism are quantified, for example, the ATP-binding cassette (ABC) transporters including subfamilies (ABCA, MDR/TAP, MRP, ALD, OABP, GCN20, White), the ATP-binding cassette transporter, sub-family A, member 1 (ABCA1) or cholesterol efflux regulatory protein (CERP) as well as various mutated forms of the ABC family. In several embodiments, the quantification of cholesterol metabolism markers is correlated with a subject's cardiovascular health and/or prognosis.

Mutations in the ABCA1 gene can cause a severe HDL-deficiency syndrome characterized by cholesterol deposition and atherosclerosis. Thus, detection of either impaired or altered expression of ABC cholesterol transporters is important to monitor atherogenesis, preferably before significant narrowing of the artery has occurred. In several embodiments, the levels of ABC transporter mRNA from a patient is compared with a known healthy range or standard for diagnosis of atherosclerotic disease. A lower or higher level of ABC transporter mRNA is indicative of disease.

Diabetes mellitus is characterized by high blood glucose levels and is a chronic disorder of fat, protein, and carbohydrate metabolism. In some cases, diabetes mellitus leads to development of or is associated with one or more types of cardiovascular disease. In a healthy individual with normal functioning metabolism insulin is produced by beta cells of the pancreas. The subsequent insulin release enables cells to absorb glucose. In contrast, in a diseased state the cells do not absorb glucose and it accumulates in the blood, leading to complications such as cardiovascular disease (coronary artery disease, peripheral vascular disease, and hypertension), retinopathy, and renal failure. Depending on the type of diabetes, a patient with diabetes either does not produce enough insulin or their cells do not properly respond to the insulin that their body does produce. In many cases, pre-diabetic individuals and/or those with diabetes live with early symptoms that are dismissed as being associated with other aspects of their lives or health. For example, post-prandial nausea may be ignored as heartburn, when in fact, the symptom is attributable to elevated blood glucose levels. Ignoring such symptoms over time can lead to, among other symptoms, excessive kidney damage prior to actual diagnosis. In several embodiments, the methods disclosed herein can be implemented in routine physical examinations to detect early markers of diabetes before the symptoms become so severe that irreversible damage is already sustained.

Several embodiments described herein are used to analyze cell-free circulating fetal nucleic acids in maternal whole blood and plasma to provide non-invasive prenatal diagnosis. Isolating or distinguishing fetally derived or cell-free nucleic acid amongst a background of maternal nucleic acid has limited the applicability of fetal diagnosis based on nucleic acid. In several embodiments, there is provided a means to capture fetal specific vesicles and RNA via capture of fetal surface markers that are present on the surface of the vesicles. Epigenetic variations between mother and fetus are also used in some embodiments.

For example, the promoter regions of tumor suppressor genes, maspin and RASSF1A are differentially methylated in the placenta compared to maternal cells. There are also RNA species that are uniquely of fetal origin such as placenta-specific 1 (PLAC1), placenta-specific 4 (PLAC4), Chorion-specific transcription factor GCM1, ZDHHC1, pregnancy-associated plasma protein A (PAPPA), pregnancy-specific beta-1-glycoprotein 9 (PSG9), tissue factor pathway inhibitor 2 (TFPI2), metastasis suppressor gene KISS1. The identification of fetal nucleic acid markers from captured vesicles links the associated disease marker to the fetus rather than to the mother. One means of linking nucleic acid to the fetus is by using single nucleotide polymorphisms or short tandem repeat polymorphisms that are present in the fetus but not the mother. One embodiment of the invention can rapidly detect fetal sex as well as single molecule, chromosomal aneuploidies, single nucleotide variations and placental microRNAs in maternal plasma. The nucleic acid analyzed may be, but is not limited to DNA, RNA, and mRNA. Examples of mRNA detected are human placental lactogen (hPL mRNA) human chorionic gonadotropin (βhCG mRNA), and corticotropin releasing hormone.

In some embodiments, fetally-derived vesicle-associated RNA is captured from maternal blood. Particular species of fetal RNA are quantified as described herein to diagnose maternal pre-eclampsia. The mRNA species may be human chorionic gonadotropin, corticotropin releasing hormone, human placental lactogen, KISS1, TPFI2, PLAC1, or GAPDH. The levels of fetally-derived RNA are compared to those of a known standard or reference. The standard or reference may be derived from vesicles from woman without pre-eclampsia. A higher or lower level of mRNA species indicates presence or risk of developing pre-eclampsia. Several embodiments are particularly advantageous because existing methods diagnosing preeclampsia may confuse the symptoms with other diseases, while several embodiments provide a definitive test to diagnose this disease.

Moreover, fetal blood sampling is, at times, performed during pregnancy for diagnosis, monitoring maternal treatment, and/or monitoring fetal problems throughout different stages of pregnancy. Fetal blood may be removed from the umbilical cord or from a fetal blood vessel such as the liver or heart. These procedures risk fetal bleeding, changes in fetal heart rate, infection, leaking of amniotic fluid, and fetal death. In several embodiments, sampling of maternal blood for fetal vesicle-associated RNA represents a safer means of obtaining a prenatal diagnosis.

Several embodiments of the methods disclosed herein provide unexpected advantages over existing diagnostic and monitoring methods. For example, chronic liver disease may have many different causes including alcoholism, hepatitis B and/or C, autoimmunity, or toxicity associated with drugs. A recognized diagnostic test for liver disease is the liver biopsy, which is typically performed via puncture of the organ with a needle. The liver biopsy technique has the associated risks such as uncontrolled bleeding and infection. The method described herein provides an opportunity to non-invasively identify RNA which indicates disease and to correlate these disease markers with liver specific markers, thus allowing the simultaneous diagnosis of a disease and identification of the diseased tissue. Several embodiments therefore provide unforeseen methods to remotely sample an organ which may either be inaccessible or present higher risks with direct sampling as compared to the benign procedure of drawing a peripheral blood sample.

As an example of markers of disease that may be organ specific, cirrhosis of the liver can present with elevated levels of aminotransferases and/or alkaline phosphatase in the blood. Several embodiments of the invention are used to concentrate vesicles in whole blood, thereby effectively concentrating a particular target marker RNA. This RNA is further subjected to high-sensitivity tests that amplify the presence of the markers, for example, PCR. The synergistic effect of concentrating target mRNA through isolation of vesicles and the specific nature and highly sensitive PCR analysis enables detection of early stages of disease prior to detection via conventional methods such as protein markers. Thus, several embodiments provide a means diagnosing disease of an internal target organ such as the liver (e.g., by measuring alkaline phosphatase RNA and correlating it to RNA for a liver-specific marker, such as hepatocyte growth factor), yet sampling whole blood without the concomitant risks associated with directly accessing the liver.

In other embodiments respiratory diseases such as pneumonia, chronic obstructive pulmonary disease, asthma, or lung cancer may be diagnosed using certain embodiments of the invention. For example, in several embodiments, RNA-associated vesicles are captured from whole blood and RNA identifying specific inflammatory molecules such as cytokines and chemokines is characterized. From this information, diagnosis of a generalized inflammatory condition can be achieved. In several embodiments, lung specific markers such as surfactant-associated proteins SP-A, AP-B, SP-D, and mucin-associated antigens are concurrently analyzed, and when correlated in the same samples, indicate lung-specific inflammation. As another example, cytokines IL-2, IL-3, IL-4, IL-5, IL-13 have been shown to have a role in asthma, as well as chemokines IL-8, RANTES, MIP-α, and eotaxin.

In addition to the organ-specific diseases disclosed above, several embodiments are used to diagnose systemic diseases. Such diseases include, but are not limited to systemic autoimmune diseases such as rheumatoid arthritis, systemic lupus erythematosus, and systemic sclerosis. These diseases often result from an overactive immune response directed towards the patient's body. In some embodiments, diagnosis of systemic lupus erythematosus is made by obtaining vesicle-associated RNA and evaluating the sample for expression of High Mobility Group Box 1 (HMGB1). Elevated levels of HMGB1 are indicative of systemic lupus erythematosus. Systemic lupus erythematosus mRNA is compared to a known standard or control and can therefore be used to diagnose or track the progression of the disease. Because systemic lupus erythematosus is characterized by a progressive immune attack on the body's cells and tissues, thereby leading to progressively greater damage to heart muscle, joints, lungs, liver, kidneys, etc., several embodiments are particularly beneficial as detection of mild forms early in the disease process help prevent more devastating tissue damage.

In several embodiments, markers may be used to identify stem cells and/or to characterize differentiated cell types. Examples of these markers include, but are not limited to, fetal liver kinase-1 (Flk1) (endothelial progenitor), smooth muscle cell-specific myosin heavy chain and vascular endothelial cell cadherin (smooth muscle cells in the wall of blood vessels); osteoblast markers such as bone-specific alkaline phosphatase, hydroxyapatite, osteocalcin (bone formation); bone marrow and blood markers such as bone morphogenetic protein receptor (mesenchymal stem and progenitor cells), CD4 and CD8 (mature T lymphocytes), CD34 (hematopoietic stem cell (HSC)), CD34+Sca1+ Lin− profile (mesencyhmal stem cell (MSC)), CD44 (mesenchymal), c-Kit (HSC, MSC), leukocyte common antigen-CD45 (white blood cell progenitor), lineage surface antigen (HSC, MSC), Mac-1 (mature granulocyte and macrophage), stem cell antigen (mesenchymal precursor cells), Thy-1 (HSC, MSC); cartilage markers such as collagens (chondrocyte), keratin (keratinocyte); adipocyte markers such as adipocyte lipid-binding protein, fatty acid transporter; liver markers such as albumin (maturing and fully differentiated hepatocytes, B-1 integrin (cell adhesion); nervous system markers such as CD133 (neural system, HSC), glial fibrillary acidic protein (astrocyte), microtubule-associated protein-2 (neuron), myelin basic protein (oligodendrocyte), nestin (neural progenitor), neural tubulin (neuron), neurofilament (neuron), noggin (neuron), O4 and O1 (oligodendrocyte), synaptophysin (neuron), tau (neuron); pancreas markers such as cytokeratin 19 (pancreatic epithelium), glucagon, insulin, insulin-promoting factor-1, pancreatic polypeptide, somatostatin (pancreatic islet), and nestin (pancreatic progenitor); pluripotent stem cell markers such as alkaline phosphatase (embryonic stem), alpha-fetoprotein, GATA-4 gene, hepatocyte nuclear factor-4, (endoderm), bone morphogenetic protein-4, brachyury (mesoderm), neuronal cell-adhesion molecule, pax6 (Ectoderm); stage-specific embryonic antigen-3 and -4, stem cell factor, telomerase, vimentin; skeletal muscle/cardiac/smooth muscle markers such as MyoD and Pax7, myogenin and MR4, myosin heavy chain, myosin light chain, stem cell marker prominin 1 (PROM1, CD133).

In some embodiments, the characterization of vesicle-associated mRNA can be used to monitor stem cell treatment. Prior to stem cell treatment, vesicle-associated mRNA from a patient is assessed for the level of stem cell marker. Subsequent to treatment of the patient, the stem cell marker is quantified. An increase in vesicle associated stem cell marker mRNA from the patient is indicative of successful grafting. Monitoring of fetally derived vesicle-associated RNA also provides a non-invasive means to monitor the success of in-utero cell transplantations.

In some embodiments of the invention the markers related to bone formation such as osteoblast marker periostin (POSTN), osteoid, type-1 collagen, Osterix, Collagen-1, bone sialoprotein, macrophage colony-stimulating factor, alkaline phosphatase, osteocalcin, osteopontin, and osteonectin.

In some embodiments of the invention the markers are related blood homeostasis such as endothelial cell marker von Willebrand factor (vWF), thrombin, factor VIII, plasmin, and fibrin. Von Willebrand factor is a plasma glycoprotein that is a mediator of platelet adhesion, as such it is released when the endothelium is damaged. VWF is involved in platelet aggregation and thrombus formation. As shown in FIG. 2F, elevated levels of von Willebrand factor are associated with an increased risk of ischemic heart disease.

In other embodiments markers associated with cell adhesion may be used to probe the state of cardiovascular pathology. Cells normally adhere to each other and to proteins of the extracellular matrix to provide a suitable environment for cell growth, differentiation, and migration. Aberrant adhesion is involved in the pathogenesis of cardiovascular disease, thrombus formation, leucocyte infiltration and the deposition of fibrotic tissue. Adhesion molecules such as integrins, selectins, and immunoglobulin superfamily members are all potentially involved in cardiac disease. For example, integrin $α_vβ_3$ is highly expressed in atherosclerotic plaques by medial and intimal smooth muscle cells and endothelial cells of angiogenic microvessels. Also, increased soluble intercellular adhesion molecule-1 (sICAM-1) is a predictor of future coronary events in patients with chronic coronary heart disease. The levels of these markers of disease can be quantified from vesicles from patients and compared to a known healthy range to diagnose disease stauts. Examples of markers of adhesion mediated cardiovascular disease include, but are not limited to, selectin (SELE), E-selectin, L-selectin, P-selectin, E-cadherins, N-cadherins, P-cadherins, T-daherins, and vascular endothelial marker cadherin 5 (CDH5).

In some embodiments markers that are evaluated are associated with liver cells such as transaminase, alkaline phosphatase, alanine amino transaminase, aspartate amino transaminase, gamma glutamyl transpeptidase, $a_1$-microglobulin/bikunin precursor, albumin, and angiotensinogen (AGT).

In other embodiments, the markers may be kidney markers Tamm-Horsfall glycoprotein (THP) also known as uromodulin, renin also known as angiotensinogenase (REN); lung markers angiotensin I converting enzyme (ACE), surfactant proteins SP-A, SP-B, SP-C, SP-D; islet markers preproinsulin (INS), glucagon, insulin, amylin, somatostatin, pancreatic polypeptide, and ghrelin; muscle markers myostatin (MSTN) or growth differentiation factor 8, activin type II receptor; inflammation markers tumor necrosis factor α (TNF), interleukin-1 (IL-1), IL-6, IL-8, interferon-γ, CC chemokines (or β-chemokines), and CXC chemokines (or α-chemokines).

In some embodiments, house keeping gene products or constitutively expressed gene products, or markers of basal cellular function can be used as markers or controls including, but not limited to, transcription factor BTF3, paired box gene 8, E3 ubiquitin-protein ligase RING1, double-stranded RNA-specific adenosine deaminase, eukaryotic translation initiation factor 3 subunit C, isoleucyl-tRNA synthetase, polyadenylate-binding protein 1, 60S ribosomal protein L3, DNA-directed RNA polymerase II subunit RPB1, peptidyl-prolyl isomerase A (cyclophilin A), core histone macro-H2A.1, death-associated protein 1, scaffold attachment factor B, glyceraldehyde 3-phosphate dehydrogenase, eolase, succinate dehydrogenase subunit A, catechol O-methyl transferase, NADH dehydrogenase [ubiquinone] 1 alpha subcomplex subunit 1, cytochrome c oxidase subunit 4 isoform 1, ATP synthase subunit alpha, proteasome subunit beta type-1, alpha-actinin-4, β actin (ACTB), β2 microglobulin (B2M), and heat shock protein 90.

In some embodiments, the status of the immune system, immune system function or the body's response to disease is measured by the amount of immune system marker mRNA. The markers may be indicative of immunodeficiency, genetic disease, autoimmune disease, or progression of infectious disease. Such markers include, but are not limited to CD16 (surface marker of NK cells), granzyme B (inducer of rapid apoptosis), and TNF-alpha (inducer of slow apoptosis). In other embodiments the immune markers include, but are not limited to CD25 (surface marker of T-reg), FoxP3 (T-reg marker), CTLA4 (Cytotoxic T-lymphocyte antigen), GARP (glycoprotein A repetitions predominant), IL-17 (putative negative regulator of T cell activation), and ARG mRNA (marker of myeloid-derived suppressor cells).

In some embodiments the marker RNA is indicative of cancer such as carcinoembryonic antigen (CEA), mucin, alpha-fetoprotein, tyrosinase, melanoma associated antigen, and mutated tumor protein 53. In some embodiments the marker RNA is indicative of specific tissue such as prostate-specific antigen (PSA) or thyroglobulin. For example CEA is produced during fetal development but stops before birth. Elevated levels of CEA are therefore not usually present in the bloodstream of healthy adults. By quantifying the level of CEA RNA in a patient and comparing it with a known healthy range or standard the presence of colorectal carcinoma, gastric carcinoma, pancreatic carcinoma, lung carcinoma and breast carcinoma, can be detected. An elevated level of CEA RNA is also indicative of tumor recurrence after removal of the tumor mass.

In other embodiments, diagnosis of infectious disease is achieved by the detection of RNA or DNA from the infectious agent that is present in vesicles of blood and body fluids. In some embodiments the infectious agent may be severe acute respiratory syndrome (SARS)-associated coronavirus, influenza, and hepatitis C, influenza A, foot-and-mouth disease virus, Human bocavirus (HBoV) and also parasites like *Trypanosoma brucei*.

Methodology

RNA present in plasma as free RNA is quickly degraded by nucleases, making it a poor diagnostic marker. As described above, some extracellular RNA is associated with particles or vesicles. This vesicle associated RNA, which includes mRNA, is protected from the degradation process in the plasma. Microvesicles are shed from most cell types and consist of fragments of plasma membrane. Microvesicles contain RNA, mRNA, microRNA, and proteins and mirror the composition of the cell from which they are shed. Exosomes are small microvesicles secreted by a wide range of mammalian cells and are secreted under normal and pathological conditions. Theses vesicles contain certain proteins and RNA including mRNA and microRNA. Exosome-like vesicles may also be found in many body fluids such as blood, urine, ascities and amniotic fluid. Aberrant expression of microRNAs has been implicated in numerous disease states, and microRNA-based therapies are under investigation. Exosomes can also be released into urine by the kidneys and their detection may serve as a diagnostic tool. The embodiments described herein may also be applied to other types of nucleic acids such as small interfering RNA (siRNA), tRNA, and small activating RNA (saRNA).

In several embodiments the RNA is used as a template to make complementary DNA (cDNA). In several embodiments, cDNA is amplified using the polymerase chain reaction (PCR). In other embodiments, amplification of nucleic acid and RNA may also be achieved by any suitable amplification technique such as nucleic acid based amplification (NASBA) or primer-dependent continuous amplification of nucleic acid, or ligase chain reaction.

In several embodiments, disease induces the expression of one or more markers, as measured by the amount of mRNA encoding said markers. In some embodiments blood is collected from a patient and erythrocytes and cellular components of the blood are removed. The patient's vesicles are concentrated by trapping them on a filter, in some embodiments. Isolated vesicles are then incubated with lysis buffer to release the RNA from the vesicles, the RNA then serving as a template for cDNA which is quantified with methods such as quantitative PCR. The level of specific marker RNA from patient vesicles is compared with a control such as, for example, RNA levels from a healthy patient population, or the RNA level from an earlier time point from the same patient or a control gene from the same patient.

In other embodiments, body fluids such as cerebrospinal fluid or urine are collected from a patient and vesicles are concentrated by trapping them on a filter. The vesicles are lysed and the RNA quantified by methods such as quantitative PCR. The level of specific RNA from the body fluid from the patient is compared to a control to determine disease status.

In some embodiments the health of a patient is monitored over time. In these embodiments, blood or body fluid is collected from a patient and the level of vesicle or particle associated RNA for a specific gene or genes is determined. A second or subsequent sample is collected from the patient and the level of specific RNA is determined. The change in health of the patient is determined by comparing the first sample RNA level with the second sample RNA level or by comparing the samples to a control or standard. In some embodiments medication may have been administered to the patient before or after the collection of the first and/or second patient sample. In some embodiments, the medication may be a drug, nutritional supplement, vitamin, immunosuppressant, anti-inflammatory drug, anesthetic or analgesic. In some embodiments the monitoring may relate to a change in nutrition such as a reduction in caloric intake, or increased hydration, or change in exercise routine, or a change in sleeping pattern of the patient.

In several embodiments, a small volume of plasma is processed to allow determination of the levels of mRNA encoding one or more disease markers in the blood. In some embodiments, the levels of mRNA encoding one or more markers will change significantly in a patient depending upon the presence or absence of disease. To determine these mRNA levels, the erythrocytes and other blood cells may be removed from the blood sample. In some embodiments, mRNA-containing vesicles are isolated from plasma using a device for isolating and amplifying mRNA. Embodiments of this device are described in more detail in U.S. patent application Ser. No. 10/796,298 (now U.S. Pat. No. 7,745, 180), Ser. Nos. 11/525,515, 11/376,018, 11/803,593, 11/803, 594, and 11/803,663, each of which is incorporated in its entirety by reference herein.

Certain embodiments of this invention further comprise a multi-well plate that contains a plurality of sample-delivery wells, a vesicle-capturing filter underneath the wells, and an mRNA capture zone underneath the filter which contains immobilized oligo(dT). In certain embodiments, the device also contains a vacuum box adapted to receive the filter plate to create a seal between the plate and the box, such that when vacuum pressure is applied, the plasma is drawn from the sample-delivery wells across the vesicle-capturing filter, thereby capturing the vesicles and allowing non-vesicle plasma components to be removed by washing the filters. In other embodiments, other means of drawing the plasma samples through the sample wells and through across the vesicle-capturing filter, such as centrifugation or positive pressure, are used. In some embodiments of the device, vesicles are captured on a plurality of filter membranes that are layered together. In several embodiments, the captured vesicles are then lysed with a lysis buffer, thereby releasing mRNA from the captured vesicles. The mRNA is then hybridized to the oligo(dT)-immobilized in the mRNA capture zone. Further detail regarding the composition of lysis buffers that may be used in several embodiments can be found in U.S. patent application Ser. No. 11/376,018, which is incorporated in its entirety by reference herein. In several embodiments, cDNA is synthesized from oligo(dT)-immobilized mRNA. In some embodiments, the cDNA is then amplified using real time PCR with primers specifically designed for amplification of disease-associated markers. Primers that are used in such embodiments are shown in Table 1. Further details about the PCR reactions used in some embodiments are also found in U.S. patent application Ser. No. 11/376,018.

detected) for one or more disease markers is quantified. In certain embodiments, quantification is calculated by comparing the amount of mRNA encoding a disease marker to a reference value. In some embodiments the reference value will be the amount of mRNA found in healthy non-diseased patients. In other embodiments, the reference value is the expression level of a house-keeping gene. In certain such embodiments, beta-actin may be used as the reference value. Numerous other house-keeping genes that are well known in the art may also be used as a reference value. In other embodiments, a house keeping gene is used as a correction factor, such that the ultimate comparison is the expression level of marker from a diseased patient as compared to the same marker from a non-diseased (control) sample. In several embodiments, the house keeping gene is a tissue

TABLE 1

Primer Sequences for RT-PCR Amplification

| Target mRNA | SEQ ID No: | Forward Sequence | SEQ ID No: | Reverse Sequence |
|---|---|---|---|---|
| ACBTB | 1 | CCTGGCACCCAGCACAAT | 2 | GCCGATCCACACGGAGTACT |
| B2M | 3 | TGACTTTGTCACAGCCCAAGATA | 4 | AATGCGGCATCTTCAAACCT |
| ADIPOQ | 5 | GCCCTGGCTGGAGTTCAGT | 6 | GCTGAGGCAGGAGAATTGCT |
| CD133 | 7 | CGGACAAAATTTAACGTTGATGTAAT | 8 | AACTGCAATCTGCACATGAAAAG |
|  | 9 | CCAGCAACGAGTCCTTCCTATAGA | 10 | CCATTCCCTGTGCGTTGAA |
| POSTN | 11 | TCAAATCGAAGAGTTGTGAACTGTT | 12 | TAATGGCTTGCGTGCATTTTA |
|  | 13 | TGAAGGTGGTGATGGTCATTTATT | 14 | TCACTGAGAACGACCTTCCCTTA |
| SELE | 15 | TGCATGGAGGGTTGTTAATGG | 16 | GGATGAAAGTGATTAAATTGTGCATAG |
|  | 17 | TCCGGGAAAGATCAACATGAG | 18 | CATTGAGCGTCCATCCTTCA |
|  | 19 | CCCTTGGTAGCTGGACTTTCTG | 20 | TTGCTTTCCGTAAGCATTTCC |
| CDH5 | 21 | ACAATGTCCAAACCCACTCATG | 22 | TGACAACAGCGAGGTGTAAAGAC |
|  | 23 | GAGGGCTCCGAGTCCATAGC | 24 | CAGTCGTTAAGGAAGTCGTAATCCA |
| VWF | 25 | CCCTGGGTTACAAGGAAGAAAAT | 26 | AGTGTCATGATCTGTCCTCCTCTTAG |
| TNF | 27 | GGAGAAGGGTGACCGACTCA | 28 | TGCCCAGACTCGGCAAAG |
| AGT | 29 | CAGAGTCTACCCAACAGCTTAACAAG | 30 | TTGATCATACACAGCAAACAGGAA |
| REN | 31 | GTGCACACTGGCCATCCA | 32 | AAACTCTGTGTAGAACTTTCGGATGA |
| ACE1 | 33 | CCGAAATACGTGGAACTCAT CAA | 34 | CACGAGTCCCCTGCATCTACA |
| INS | 35 | CATTGTGGAACAATGCTGTACCA | 36 | GCCTGCGGGCTGCGTCTA |
| MSTN | 37 | CCTCTAACTGTGGATTTTGAAGCTT | 38 | CTCCAGAGCAGTAATTGGCCTTA |
| ABCA1 | 39 | CCTCAGTTTGATGCCATCACA | 40 | TCCTCTCAAAAGGGCAAAGAAC |
| CCL8 | 41 | AGAGCTACACAAGAATCACCAACATC | 42 | AGACCTCCTTGCCCCGTTT |
| TGFB1 | 43 | CTGCTGAGGCTCAAGTTAAAAGTG | 44 | TGAGGTATCGCCAGGAATTGT |
| HBA2 | 45 | GCCCTGGAGAGGATGTTCCT | 46 | CGTGGCTCAGGTCGAAGTG |
| THBS1 | 47 | CGTCACATAGGCTGGAAAGATTT | 48 | CACTCTAATGAAACCCGTCTTTGG |
| ITGA2B | 49 | TGCTGCTGCTCACCATCCT | 50 | CCGGTTCCGCTTGAAGAAG |
| PFKP | 51 | CCTGTGGCAGAGCTGAAGAAG | 52 | GCTTGAGCCACCACTGTTCTTT |
| FABP4 | 53 | GGAAAATCAACCACCATAAAGAGAA | 54 | GGAAGTGACGCCTTTCATGAC |
| LPL | 55 | CAGCATAATTCGGAAGGGAAAAC | 56 | GCACGATCATCTCTCTCAGAGAAA |

After the completion of the PCR reaction, the mRNA (as represented by the amount of PCR-amplified cDNA specific gene or marker, such as those discussed above. In still other embodiments, the reference value is zero, such that the quantification of the markers is represented by an absolute number. In several embodiments a ratio comparing the expression of one or more markers from a diseased patient to one or more other markers from a non-diseased person is made.

In several other embodiments, marker expression is measured before and/or after administration of a drug to a patient. In such embodiments, the expression profiles may be used to predict the efficacy of a drug compound or to monitor side effects of the drug compound. In some embodiments the drug monitored may have been administered to treat atherosclerosis, hypertension, cardiovascular diseases, obesity, hypercholesterolemia, diabetes, or collagen diseases. In other embodiments the treatment may be an anti-cancer drug or an immunosuppressant drug. In some embodiments, a drug compound will induce the expression of a distinctive mRNA profile. Likewise, in other embodiments, a drug may inhibit one or more markers. In some such embodiments, the efficacy of drug treatment can be monitored by the disappearance of markers associated with a particular disease state.

The mRNA analyses described herein are applicable to humans in some embodiments, but in other are applicable to animals. In addition to blood-derived vesicles, the method can be applied to blood-borne bacterial and viral markers. Thus, several embodiments are useful in the diagnosis and identification of the tissue location of infections. By selecting appropriate mRNAs, and organ/tissue/cell specific damages or pathological conditions (such as obesity, metabolic diseases, inflammation, infection, cancer, etc.), a qualitative and quantitative assessment can be made of the RNA and of the disease state. The mRNA assay can be applied to lesions where appropriate markers are not yet identified. The method can also be applied to lesions, cell damage, and homeostatic states in a range of organs and cell types such as lung, pancreas, adipose tissue, muscle, bone/joint/cartilage, stomach, intestine, endothelial cells, brain, etc. Furthermore, localization of damages within an organ (glomerulus, proximal/distal tubules in kidney, bronchiole, trachea, type 2 cells in lung, cortex, cerebellum, hippocampus in brain, α-, β-, and δ-cells in pancreas, etc.) is possible in several embodiments, by use of cell-specific mRNA.

EXAMPLES

Specific embodiments will be described with reference to the following examples which should be regarded in an illustrative rather than a restrictive sense.

Example 1

Measurement of Naked RNA in Plasma

In order to evaluate stability of extracellular RNA species, a synthetic RNA standard was exposed to plasma to assess the degradation by RNAses. The stability of naked RNA in plasma was assessed by comparing RNA which had been exposed to plasma to unexposed RNA. Both samples were then quantified to determine the amount RNA degradation in response to plasma exposure. The incubation of naked RNA with plasma shows the high instability and rapid degradation of naked RNA in the blood.

Briefly, a 109 base long synthetic RNA was first incubated with human plasma for 5 min, and then suspended in Lysis buffer (0.5% N-Lauroylsarcosine, 4× standard saline citrate, 10 mM Tris-HCl (pH 7.4), 1 mM EDTA, 0.1% IGEPAL CA-630, 1.79 M guanidine thiocyanate, 1% 2-mercaptoethanol, 0.5 mg/ml proteinase K, 10 mg/ml sonicated salmon sperm DNA, 10 mg/ml *Escherichia coli* tRNA 0.5% N-Lauroylsarcosine, 4× standard saline citrate, 10 mM Tris-HCl (pH 7.4), 1 mM EDTA, 0.1% IGEPAL CA-630, 1.79 M guanidine thiocyanate, 1% 2-mercaptoethanol, 0.5 mg/ml proteinase K, 10 mg/ml sonicated salmon sperm DNA, 10 mg/ml *Escherichia coli* tRNA). As a control, a separate sample of synthetic RNA was directly suspended in Lysis buffer. Both samples were then used to quantify RNA using real time PCR using iTaq SYBR (BioRad, Hercules, Calif.) as fully described below. As shown in FIG. 1, the amount of synthetic RNA from the plasma-treated sample (FIG. 1, right) was significantly less than that of the control (FIG. 1, left) with a ΔCt of around 6 (½6=¹⁄64), suggesting that naked RNA was digested quickly in plasma. Despite this rapid degradation, in certain embodiments, isolation and quantification of naked RNA is performed.

Example 2

Ex Vivo Screening of mRNA Species for Detection of Vascular Disease

In order to demonstrate the efficacy and sensitivity of several embodiments of the methods disclosed herein, expression of disease markers from blood samples from patients with vascular disease were compared with healthy patients. Several markers related to vascular disease were used to validate the method and ensure that it could be applied to a wide range of disease states using the protocol. Controls, such as β-actin and β2-microglobulin were used and the patient histories were correlated with disease marker RNAs.

Triplicate aliquots of 200 µL of plasma were applied to a vesicle capturing filterplate (as described above), and centrifuged at 2,000×g for 5 minutes to trap vesicles on the membrane. After centrifugation, 50 µL of Lysis Buffer was added to each well which were then incubated at 37° C. for 10 minutes to lyse the vesicles. The Lysis buffer was supplemented with 5 nM of reverse primers and/or antisense primers of target genes. The Lysis buffer was also optionally supplemented with synthetic RNA which served as a control. The filterplate was then placed onto a 96-well oligo (dT)-immobilized plate (GENEPLATE®) and centrifuged at 2,000×g for 5 minutes to transfer vesicle lysate to the GENEPLATE®. After centrifugation, the GENEPLATE® was placed in a refrigerator overnight for the hybridization between oligo(dT) and polyA-tails of mRNA. The GENEPLATE® was then washed 6 times with 150 µL of Wash Buffer (0.5 M NaCl, 10 mM Tris (pH 7.4), 1 mM EDTA). The cDNA was synthesized at 37° C. for 2 hours by addition to each well of 30 µL of reverse transcription buffer (50 mM KCl, 10 mM Tris-HCl (pH 8.3), 5.5 mM MgCl$_2$, 0.1% Tween 20) supplemented with 1.25 mM of each deoxynucleoside triphosphate, 4 units of rRNasin, and 80 U of MMLV reverse transcriptase.

The cDNA solution was then used for real time PCR using iTaq SYBR (BioRad, Hercules, Calif.). An aliquot of cDNA was mixed with an equal volume of 2× reaction mix containing 0.4 mM each of dATP, dCTP, dGTP, and dTTP, 50 U/ml iTaq DNA polymerase, 6 mM Mg2+, SYBR Green I, ROX reference dye, stabilizers. This mixture was supplemented with forward and reverse gene specific primers. The cycle threshold (Ct), at which fluorescence exceeded background levels, was determined by analysis with SDS software (Applied Biosystems). The Ct value was used to calculate the original relative amount of the marker mRNA.

The plasma used for FIG. 2 was obtained from three adult type 2 diabetes patients with morbid obesity and three healthy adult volunteers. The plasma samples were subjected to the methods disclosed herein for quantifying various mRNA disease markers. Diabetes patient #1 was a 72 year old male African American with morbid obesity (294 lb and 5'7"), atrial fibrillation, hyperlipidemia, hypertension, anemia, and vitamin D deficiency, with a history of heart bypass surgery. Diabetes patient #2 was a 57 year old male African American with morbid obesity (322 lb and 5'7"), hypertension, hypercholesterolemia, and glaucoma. Diabetes patient #3 was a 45 year old female Caucasian with morbid obesity (213½ lb and 5'3"), hypertension, and hypercholesterolemia. Control subject #1 was a 52 year old female Caucasian, control subject #2 was a 41 year old female Caucasian, and control subject #3 was a 48 year old female Caucasian.

Figure 2A:
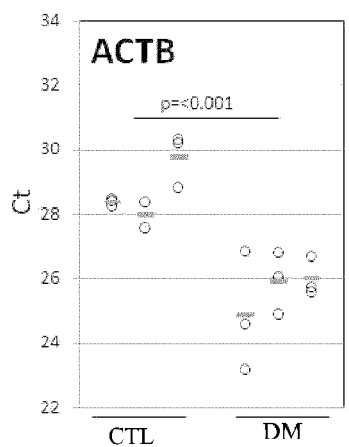
FIGS. 2A-2N depict ex vivo screening of various mRNA species for detection of vascular disease. Samples are labeled as either being CTL (control) or DM (DM/obesity). Each symbol is the mean of triplicate plasma samples in each subject tested.
Figure 2B:
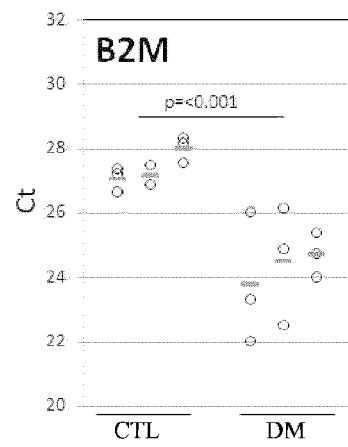
Figure 2C:
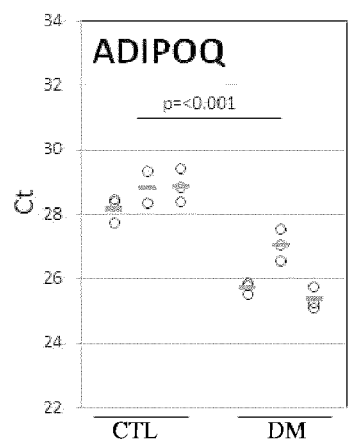
Figure 2D:
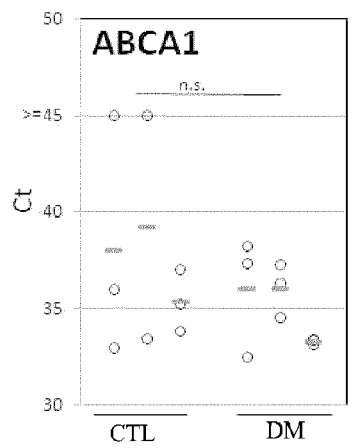
Figure 2E:
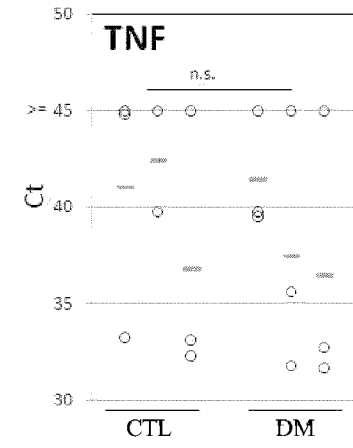
Figure 2F:
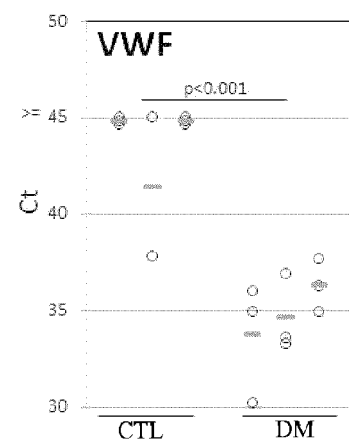

As can be seen in FIGS. 2A and 2B, housekeeping genes β-Actin (ACTB) and β2 microglobulin (B2M) were present in both control and diabetes/obesity patients' plasma, and the expression levels of these genes were significantly ($p<0.001$) higher in diabetes patients compared to the control. Thus, in several embodiments, these (or other) house keeping genes function as internal controls within a disease-having population or within an individual subject over time. In some embodiments, certain housekeeping genes that do not display alterations in expression between the control and diseased states are used. Adipose tissue marker ADIPOQ (FIG. 2C) and ABCA1 (FIG. 2D) mRNA were also present in both groups, however, the levels of ADIPOQ mRNA were significantly ($p<0.001$) higher in diabetes patients compared to the control, whereas the levels of ABCA1 were unchanged between the two groups. The discrepancy between ADIPOQ and ABCA1 may be explained by the fact that ABCA1 is not adipose tissue specific compared to ADIPOQ. Thus, in certain embodiments, characterization of ADIPOQ is used as a diagnostic indicator of obesity related disease.

Endothelium marker vWF mRNA was not present in control plasma except 1 of 3 aliquots in subject #2, whereas all diabetes patients showed amplification of VWF mRNA (FIG. 2F). Thus, in several embodiments, the presence of vWF expression in the whole blood is indicative of a vascular disease condition. Other endothelium markers, such as SELE and CDH5 were not detected. Moreover, stem cell marker CD133, osteoblast marker POSTN, liver marker AGT, kidney marker REN, lung marker ACE, islet marker INS, muscle marker MSTN were not detected. Although the inflammation marker TNF was detected from both groups (FIG. 2E), the expression levels of TNF were unchanged between the two groups.

Additionally, as shown in FIG. 2G, the levels of erythrocyte-derived HBA2 mRNA were not different between the control and diabetes groups. These data suggest hemolysis of blood samples during collection and processing is negligible. Such data bolster the validity of data wherein changes are detected, as sample to sample variation due to processing is minimal. Moreover, levels of ITGA2B and PFKP (platelet-specific mRNAs; FIGS. 2H and 2I, respectively) were not different, also suggesting that the contamination of platelets into plasma samples were not significantly different between the two groups. THBS1 is a marker of platelets and/or endothelial cells. Levels of THBS1 were slightly higher in DM group, but not statistically significant. However, in some embodiments, increased levels of THBS1 are indicative of a vascular disease or damage.

As discussed above, the vascular inflammatory response involves interactions between inflammatory cells (neutrophils, lymphocytes, monocytes, macrophages), endothelial cells, vascular smooth muscle cells, and extracellular matrix. Thus, a wide variety of markers may be indicative of injury or disease. For example, in several embodiments, vascular injury is associated with increased expression of adhesion molecules by endothelial cells and/or recruitment of inflammatory cells, growth factors, and cytokines. Cytokines include, but are not limited to, tumor necrosis factors, interleukins, lymphokines, monokines, interferons, colony stimulating factors, and transforming growth factors. Persistent increases in cytokines may be associated with vascular dysfunction and vascular disease such as atherosclerosis, obesity, abdominal aortic aneurysm, varicose veins and hypertension. As shown in FIGS. 2K and 2L, two inflammatory cytokines (IL8 and TGFB, respectively) showed differing patterns of expression. Levels of IL8 were lower in diabetic patients as compared to controls. However, TGFB was higher in diabetic samples. The differences in expression between the two different markers may reflect the different roles of IL8 and TGFB in the development and progression of diabetes in the subjects tested. For example, IL8 has been shown to be produced and released from human adipose tissue and/or adipocytes and to inhibit the phosphorylation of Akt, which is involved in the initiation of several of insulin's metabolic effects, including glucose uptake and GLUT-4 translocation. Thus, IL-8 may be involved in the development of insulin resistance, which is involved in development of Type 2 diabetes, which is common in obese individuals. As such, in the subjects tested, IL8 levels may not be significantly different from control due to the fact the diabetes has already developed and been diagnosed in the subjects tested. Thus, in several embodiments, IL8 levels may be useful as an early marker of diabetes, the associated vascular injuries and/or atherosclerosis. In contrast, TGFB levels were significantly increased in the diabetic samples. TGFB has been implicated, for example, in the development of kidney damage and sclerosis that results from diabetes. Thus, in several embodiments, TGFB levels show a greater difference in expression (versus control) when diabetes is established in a subject (as opposed to during the development of the disease, as with IL8 in some embodiments). Thus, in some embodiments, TGFB is used as a marker of monitoring the severity of diabetes, or its associated kidney and/or vascular damage. In some embodiments, TGBF levels are also used to monitor the progression of the disease and/or monitor the efficacy of treatment of the disease.

As shown in FIGS. 2M and 2N, respectively, one of two adipose tissue-specific mRNAs (fatty acid binding protein 4, FABP4) was significantly elevated in diabetes, but LPL (lipoprotein lipase) was not. FABP4 is one member of a family of carrier proteins that facilitate the transfer of fatty acids between extracellular and intracellular membranes of cells. Elevated circulating FABP levels are indicative of tissue damage. For example, increased FABP has been associated with disorders of lipid metabolism and atherosclerosis, based on the resultant increased uptake of fatty acids. Both lipid metabolism disruption and atherosclerosis are common in diabetes, particularly in obese diabetic subjects. Thus, in several embodiments, increased FABP4 (as well as other family members, depending on the embodiment) are used as markers tissue damage, vascular disease, and/or diabetes. As discussed above, based on its increased expression in established disease states such as diabetes, in several embodiments, FABP4 is used as a marker of monitoring the severity of diabetes, or its associated atherosclerosis and/or vascular damage. In some embodiments, FABP4 levels are also used to monitor the progression of the disease and/or monitor the efficacy of treatment of the disease. LPL was not significantly different between control and diabetic subjects (FIG. 2N). LPL deficiency leads to hypertriglyceridemia (elevated levels of triglycerides in the bloodstream). Often, diets high in refined carbohydrates have been shown to cause tissue-specific overexpression of LPL, which is not only associated with obesity, but also with tissue-specific insulin resistance and consequent development of type 2 diabetes mellitus. Thus, as with IL8 above, in several embodiments, LPL is used as a marker of developing diabetes, obesity, or the consequent vascular side effects due to elevated lipid levels.

Thus, the discrepancies between certain markers within a family (e.g., adipose tissue-specific markers) may, in several embodiments, be indicative of differential roles of the various markers in certain stages of a disease (e.g., developing disease, established disease, etc.).

These data suggest that the mRNA present in the vesicles reflects specific physiological or pathological conditions, and not random events. For example, the detection of endothelial cell marker VWF and adipose tissue marker ADIPOQ in plasma can serve as a diagnostic for vascular diseases and obesity-related health problems. The detection of elevated levels of TGFB or FABP4 can serve also serve similar functions for obese and/or diabetic patients at risk or suffering from vascular injury or damage. Moreover, data that is not significantly different between diabetic subjects and control subjects (such as HBA2, ITGA2B and PFKP) indicates that those results that are different are specific disease or injury-induced changes, and not artifacts of the processing and analysis protocols.

Various embodiments of the present invention have been described above. Although this invention has been described with reference to these specific embodiments, the descriptions are intended to be illustrative of the invention and are not intended to be limiting. Various modifications and applications may occur to those skilled in the art without departing from the true spirit and scope of the invention as defined in the appended claims.

What is claimed is:

1. A method for administering a medication to a human patient having a vascular disease, the method comprising:
    (A) having a first sample of a biological fluid from the patient sent to a laboratory, wherein said sample comprises vesicles comprising RNA, for the laboratory to perform an assay comprising the following steps (1)-(8):
        (1) capturing vesicles from said sample, wherein said capturing comprises:
            (a) loading at least a portion of said first sample of biological fluid into a sample loading region of a vesicle capture device;
            (b) passing said sample from said sample loading region through a vesicle-capture material in said vesicle capture device, said vesicle-capture material comprising a plurality of layers of glassfiber, thereby producing a supernatant,
            wherein said plurality of layers of glassfiber comprises at least a first layer and a second layer of glassfiber, and
            wherein said first layer of glassfiber is configured to capture material from said sample that is about 1.6 microns or greater in diameter, and wherein said second layer of glassfiber is configured to capture vesicles having a minimum size from about 0.6 microns to about 0.8 microns in diameter, and having a maximum size of less than 1.6 microns; and
            (c) passing said supernatant to a sample receiving region of said vesicle capture device,
            wherein said passings result in capture of said vesicles from said sample on or in said vesicle-capture material, thereby capturing said vesicles;
        (2) lysing said captured vesicles to release said RNA from said captured vesicles, wherein said RNA from said captured vesicles comprises a first, vascular disease-specific RNA and a second, endothelial cell-specific RNA, wherein said first RNA and said second RNA are different, and wherein said vascular disease is selected from the group consisting of atherosclerosis, hypertension, adhesion-medicated cardiovascular disease, and hypercholesterolemia;

(3) quantifying said first RNA from said sample by a method selected from the group consisting of reverse-transcription polymerase chain reaction (RT-PCR), real-time RT-PCR, northern blotting, fluorescence activated cell sorting, ELISA, and mass spectrometry;

(4) comparing the quantity of said first RNA from said sample to the quantity of a corresponding first RNA from healthy subjects;

(5) determining a difference between the quantity of said first RNA from said sample as compared to the quantity of said corresponding first RNA from said healthy subjects, wherein the said difference indicates a diseased state in said patient;

(6) quantifying said second RNA from said sample by a method selected from the group consisting of reverse-transcription polymerase chain reaction (RT-PCR), real-time RT-PCR, northern blotting, fluorescence activated cell sorting, ELISA, and mass spectrometry;

(7) comparing the quantity of said second RNA from said sample to the quantity of a corresponding second RNA from subjects without said vascular disease;

(8) determining that there is a greater quantity of said second RNA as compared to the quantity of said corresponding second RNA from said subjects without said vascular disease, wherein said greater quantity indicates that said patient has said vascular disease; and (B) administering a medication for treatment of said vascular disease to said patient.

2. The method of claim 1, wherein said biological fluid comprises a biological fluid selected from the group consisting of whole blood, blood plasma, serum, and cerebrospinal fluid.

3. The method of claim 2, wherein said biological fluid comprises whole blood and said method further comprises removing erythrocytes and cellular blood components from said whole blood prior to the capturing of the vesicles from said sample.

4. The method of claim 1, wherein said second RNA is selected from the group consisting of: mRNA, microRNA, snRNA, and poly(A)+RNA and said first RNA is selected from the group consisting of: mRNA, microRNA, snRNA, and poly(A)+RNA.

5. The method of claim 1, wherein said first RNA is from endothelial cells.

6. The method of claim 1, wherein said first RNA is from atherosclerotic plaques.

7. The method of claim 1, wherein said first RNA encodes von Willebrand factor (vWF).

8. The method of claim 1, wherein said second RNA encodes von Willebrand factor (vWF).

9. The method of claim 1, wherein said first RNA comprises one or more markers selected from the group consisting of IL-5, IL-8, IL-13, RANTES, MIP-$\alpha$, and eotaxin.

10. The method of claim 1, wherein said vascular disease is hypertension and wherein said first RNA is selected from the group consisting of high-sensitivity C-reactive protein and soluble E-selectin.

11. The method of claim 1, wherein either said first or said second RNA encodes thrombospondin1 (THBS1).

12. The method of claim 1, wherein said first RNA comprises one or more markers of hypercholesterolemia, wherein said markers are selected from the group consisting of ATP-binding cassette (ABC) transporter ABCA GCN20, ATP-binding cassette (ABC) transporter ABCA white, the ATP-binding cassette transporter, sub-family A, member 1 (ABCA1) and cholesterol efflux regulatory protein (CERP).

13. The method of claim 1, wherein said vascular disease comprises an imbalance in blood homeostasis and said first RNA is selected from the group consisting of von Willebrand factor (vWF), thrombin, factor VIII, plasmin, and fibrin.

14. The method of claim 1, wherein said first RNA comprises one or more markers of adhesion mediated cardiovascular disease, wherein said markers are selected from the group consisting of selectin (SELE), E-selectin, L-selectin, P-selectin, and vascular endothelial marker cadherin 5 (CDH5).

* * * * *

SEQUENCE LISTING

<160> NUMBER OF SEQ ID NOS: 56

<210> SEQ ID NO 1
<211> LENGTH: 18
<212> TYPE: DNA
<213> ORGANISM: Homo sapiens
<220> FEATURE:
<221> NAME/KEY: misc_feature
<223> OTHER INFORMATION: Forward primer for beta-actin

<400> SEQUENCE: 1
cctggcaccc agcacaat                                                 18

<210> SEQ ID NO 2
<211> LENGTH: 20
<212> TYPE: DNA
<213> ORGANISM: Homo sapiens
<220> FEATURE:
<221> NAME/KEY: misc_feature
<223> OTHER INFORMATION: Reverse primer for beta-actin

<400> SEQUENCE: 2
gccgatccac acggagtact                                               20

<210> SEQ ID NO 3
<211> LENGTH: 23
<212> TYPE: DNA
<213> ORGANISM: Homo sapiens
<220> FEATURE:
<221> NAME/KEY: misc_feature
<223> OTHER INFORMATION: Forward primer for beta-2 microglobulin

<400> SEQUENCE: 3
tgactttgtc acagcccaag ata                                           23

<210> SEQ ID NO 4
<211> LENGTH: 20
<212> TYPE: DNA
<213> ORGANISM: Homo sapiens
<220> FEATURE:
<221> NAME/KEY: misc_feature
<223> OTHER INFORMATION: Reverse primer for beta-2 microglobulin

```
<400> SEQUENCE: 4
aatgcggcat cttcaaacct                                               20

<210> SEQ ID NO 5
<211> LENGTH: 19
<212> TYPE: DNA
<213> ORGANISM: Homo sapiens
<220> FEATURE:
<221> NAME/KEY: misc_feature
<223> OTHER INFORMATION: Forward primer for ADIPOQ

<400> SEQUENCE: 5
gccctggctg gagttcagt                                                19

<210> SEQ ID NO 6
<211> LENGTH: 20
<212> TYPE: DNA
<213> ORGANISM: Homo sapiens
<220> FEATURE:
<221> NAME/KEY: misc_feature
<223> OTHER INFORMATION: Reverse primer for ADIPOQ

<400> SEQUENCE: 6
gctgaggcag gagaattgct                                               20

<210> SEQ ID NO 7
<211> LENGTH: 26
<212> TYPE: DNA
<213> ORGANISM: Homo sapiens
<220> FEATURE:
<221> NAME/KEY: misc_feature
<223> OTHER INFORMATION: Forward primer 1 for CD133

<400> SEQUENCE: 7
cggacaaaat ttaacgttga tgtaat                                        26

<210> SEQ ID NO 8
<211> LENGTH: 23
<212> TYPE: DNA
<213> ORGANISM: Homo sapiens
<220> FEATURE:
<221> NAME/KEY: misc_feature
<223> OTHER INFORMATION: Reverse primer 1 for CD133

<400> SEQUENCE: 8
aactgcaatc tgcacatgaa aag                                           23

<210> SEQ ID NO 9
<211> LENGTH: 24
<212> TYPE: DNA
<213> ORGANISM: Homo sapiens
<220> FEATURE:
<221> NAME/KEY: misc_feature
<223> OTHER INFORMATION: Forward primer 2 for CD133

<400> SEQUENCE: 9
ccagcaacga gtccttccta taga                                          24

<210> SEQ ID NO 10
<211> LENGTH: 19
<212> TYPE: DNA
<213> ORGANISM: Homo sapiens
<220> FEATURE:
<221> NAME/KEY: misc_feature
<223> OTHER INFORMATION: Reverse primer 2 for CD133
```

<400> SEQUENCE: 10
ccattccctg tgcgttgaa                                          19

<210> SEQ ID NO 11
<211> LENGTH: 25
<212> TYPE: DNA
<213> ORGANISM: Homo sapiens
<220> FEATURE:
<221> NAME/KEY: misc_feature
<223> OTHER INFORMATION: Forward primer 1 for POSTN

<400> SEQUENCE: 11
tcaaatcgaa gagttgtgaa ctgtt                                   25

<210> SEQ ID NO 12
<211> LENGTH: 21
<212> TYPE: DNA
<213> ORGANISM: Homo sapiens
<220> FEATURE:
<221> NAME/KEY: misc_feature
<223> OTHER INFORMATION: Reverse primer 1 for POSTN

<400> SEQUENCE: 12
taatggcttg cgtgcatttt a                                       21

<210> SEQ ID NO 13
<211> LENGTH: 24
<212> TYPE: DNA
<213> ORGANISM: Homo sapiens
<220> FEATURE:
<221> NAME/KEY: misc_feature
<223> OTHER INFORMATION: Forward primer 2 for POSTN

<400> SEQUENCE: 13
tgaaggtggt gatggtcatt tatt                                    24

<210> SEQ ID NO 14
<211> LENGTH: 23
<212> TYPE: DNA
<213> ORGANISM: Homo sapiens
<220> FEATURE:
<221> NAME/KEY: misc_feature
<223> OTHER INFORMATION: Reverse primer 2 for POSTN

<400> SEQUENCE: 14
tcactgagaa cgaccttccc tta                                     23

<210> SEQ ID NO 15
<211> LENGTH: 21
<212> TYPE: DNA
<213> ORGANISM: Homo sapiens
<220> FEATURE:
<221> NAME/KEY: misc_feature
<223> OTHER INFORMATION: Forward primer 1 for SELE

<400> SEQUENCE: 15
tgcatggagg gttgttaatg g                                       21

<210> SEQ ID NO 16
<211> LENGTH: 27
<212> TYPE: DNA
<213> ORGANISM: Homo sapiens
<220> FEATURE:
<221> NAME/KEY: misc_feature
<223> OTHER INFORMATION: Reverse primer 1 for SELE -continued

```
<400> SEQUENCE: 16
ggatgaaagt gattaaattg tgcatag                                          27

<210> SEQ ID NO 17
<211> LENGTH: 21
<212> TYPE: DNA
<213> ORGANISM: Homo sapiens
<220> FEATURE:
<221> NAME/KEY: misc_feature
<223> OTHER INFORMATION: Forward primer 2 for SELE

<400> SEQUENCE: 17
tccgggaaag atcaacatga g                                                21

<210> SEQ ID NO 18
<211> LENGTH: 20
<212> TYPE: DNA
<213> ORGANISM: Homo sapiens
<220> FEATURE:
<221> NAME/KEY: misc_feature
<223> OTHER INFORMATION: Reverse primer 2 for SELE

<400> SEQUENCE: 18
cattgagcgt ccatccttca                                                  20

<210> SEQ ID NO 19
<211> LENGTH: 22
<212> TYPE: DNA
<213> ORGANISM: Homo sapiens
<220> FEATURE:
<221> NAME/KEY: misc_feature
<223> OTHER INFORMATION: Forward primer 3 for SELE

<400> SEQUENCE: 19
cccttggtag ctggactttc tg                                               22

<210> SEQ ID NO 20
<211> LENGTH: 21
<212> TYPE: DNA
<213> ORGANISM: Homo sapiens
<220> FEATURE:
<221> NAME/KEY: misc_feature
<223> OTHER INFORMATION: Reverse primer 3 for SELE

<400> SEQUENCE: 20
ttgctttccg taagcatttc c                                                21

<210> SEQ ID NO 21
<211> LENGTH: 22
<212> TYPE: DNA
<213> ORGANISM: Homo sapiens
<220> FEATURE:
<221> NAME/KEY: misc_feature
<223> OTHER INFORMATION: Forward primer 1 for CDH5

<400> SEQUENCE: 21
acaatgtcca aacccactca tg                                               22

<210> SEQ ID NO 22
<211> LENGTH: 23
<212> TYPE: DNA
<213> ORGANISM: Homo sapiens
<220> FEATURE:
<221> NAME/KEY: misc_feature
<223> OTHER INFORMATION: Reverse primer 1 for CDH5
```

-continued

<400> SEQUENCE: 22
tgacaacagc gaggtgtaaa gac                                          23

<210> SEQ ID NO 23
<211> LENGTH: 20
<212> TYPE: DNA
<213> ORGANISM: Homo sapiens
<220> FEATURE:
<221> NAME/KEY: misc_feature
<223> OTHER INFORMATION: Forward primer 2 for CDH5

<400> SEQUENCE: 23
gagggctccg agtccatagc                                              20

<210> SEQ ID NO 24
<211> LENGTH: 25
<212> TYPE: DNA
<213> ORGANISM: Homo sapiens
<220> FEATURE:
<221> NAME/KEY: misc_feature
<223> OTHER INFORMATION: Reverse primer 2 for CDH5

<400> SEQUENCE: 24
cagtcgttaa ggaagtcgta atcca                                        25

<210> SEQ ID NO 25
<211> LENGTH: 23
<212> TYPE: DNA
<213> ORGANISM: Homo sapiens
<220> FEATURE:
<221> NAME/KEY: misc_feature
<223> OTHER INFORMATION: Forward primer for VWF

<400> SEQUENCE: 25
ccctgggtta caaggaagaa aat                                          23

<210> SEQ ID NO 26
<211> LENGTH: 26
<212> TYPE: DNA
<213> ORGANISM: Homo sapiens
<220> FEATURE:
<221> NAME/KEY: misc_feature
<223> OTHER INFORMATION: Reverse primer for VWF

<400> SEQUENCE: 26
agtgtcatga tctgtcctcc tcttag                                       26

<210> SEQ ID NO 27
<211> LENGTH: 20
<212> TYPE: DNA
<213> ORGANISM: Homo sapiens
<220> FEATURE:
<221> NAME/KEY: misc_feature
<223> OTHER INFORMATION: Forward primer for TNF

<400> SEQUENCE: 27
ggagaagggt gaccgactca                                              20

<210> SEQ ID NO 28
<211> LENGTH: 18
<212> TYPE: DNA
<213> ORGANISM: Homo sapiens
<220> FEATURE:
<221> NAME/KEY: misc_feature
<223> OTHER INFORMATION: Reverse primer for TNF

<400> SEQUENCE: 28
tgcccagact cggcaaag                                              18

<210> SEQ ID NO 29
<211> LENGTH: 26
<212> TYPE: DNA
<213> ORGANISM: Homo sapiens
<220> FEATURE:
<221> NAME/KEY: misc_feature
<223> OTHER INFORMATION: Forward primer for AGT

<400> SEQUENCE: 29
cagagtctac ccaacagctt aacaag                                     26

<210> SEQ ID NO 30
<211> LENGTH: 24
<212> TYPE: DNA
<213> ORGANISM: Homo sapiens
<220> FEATURE:
<221> NAME/KEY: misc_feature
<223> OTHER INFORMATION: Reverse primer for AGT

<400> SEQUENCE: 30
ttgatcatac acagcaaaca ggaa                                       24

<210> SEQ ID NO 31
<211> LENGTH: 18
<212> TYPE: DNA
<213> ORGANISM: Homo sapiens
<220> FEATURE:
<221> NAME/KEY: misc_feature
<223> OTHER INFORMATION: Forward primer for REN

<400> SEQUENCE: 31
gtgcacactg gccatcca                                              18

<210> SEQ ID NO 32
<211> LENGTH: 26
<212> TYPE: DNA
<213> ORGANISM: Homo sapiens
<220> FEATURE:
<221> NAME/KEY: misc_feature
<223> OTHER INFORMATION: Reverse primer for REN

<400> SEQUENCE: 32
aaactctgtg tagaactttc ggatga                                     26

<210> SEQ ID NO 33
<211> LENGTH: 23
<212> TYPE: DNA
<213> ORGANISM: Homo sapiens
<220> FEATURE:
<221> NAME/KEY: misc_feature
<223> OTHER INFORMATION: Forward primer for ACE1

<400> SEQUENCE: 33
ccgaaatacg tggaactcat caa                                        23

<210> SEQ ID NO 34
<211> LENGTH: 21
<212> TYPE: DNA
<213> ORGANISM: Homo sapiens
<220> FEATURE:
<221> NAME/KEY: misc_feature
<223> OTHER INFORMATION: Reverse primer for ACE1

<400> SEQUENCE: 34
cacgagtccc ctgcatctac a                                              21

<210> SEQ ID NO 35
<211> LENGTH: 23
<212> TYPE: DNA
<213> ORGANISM: Homo sapiens
<220> FEATURE:
<221> NAME/KEY: misc_feature
<223> OTHER INFORMATION: Forward primer for INS

<400> SEQUENCE: 35
cattgtggaa caatgctgta cca                                            23

<210> SEQ ID NO 36
<211> LENGTH: 18
<212> TYPE: DNA
<213> ORGANISM: Homo sapiens
<220> FEATURE:
<221> NAME/KEY: misc_feature
<223> OTHER INFORMATION: Reverse primer for INS

<400> SEQUENCE: 36
gcctgcgggc tgcgtcta                                                  18

<210> SEQ ID NO 37
<211> LENGTH: 25
<212> TYPE: DNA
<213> ORGANISM: Homo sapiens
<220> FEATURE:
<221> NAME/KEY: misc_feature
<223> OTHER INFORMATION: Forward primer for MSTN

<400> SEQUENCE: 37
cctctaactg tggattttga agctt                                          25

<210> SEQ ID NO 38
<211> LENGTH: 23
<212> TYPE: DNA
<213> ORGANISM: Homo sapiens
<220> FEATURE:
<221> NAME/KEY: misc_feature
<223> OTHER INFORMATION: Reverse primer for MSTN

<400> SEQUENCE: 38
ctccagagca gtaattggcc tta                                            23

<210> SEQ ID NO 39
<211> LENGTH: 21
<212> TYPE: DNA
<213> ORGANISM: Homo sapiens
<220> FEATURE:
<221> NAME/KEY: misc_feature
<223> OTHER INFORMATION: Forward primer for ABCA1

<400> SEQUENCE: 39
cctcagtttg atgccatcac a                                              21

<210> SEQ ID NO 40
<211> LENGTH: 22
<212> TYPE: DNA
<213> ORGANISM: Homo sapiens
<220> FEATURE:
<221> NAME/KEY: misc_feature
<223> OTHER INFORMATION: Reverse primer for ABCA1

<400> SEQUENCE: 40
tcctctcaaa agggcaaaga ac                                    22

<210> SEQ ID NO 41
<211> LENGTH: 26
<212> TYPE: DNA
<213> ORGANISM: Homo sapiens
<220> FEATURE:
<221> NAME/KEY: misc_feature
<223> OTHER INFORMATION: Forward primer for CCL8

<400> SEQUENCE: 41
agagctacac aagaatcacc aacatc                                26

<210> SEQ ID NO 42
<211> LENGTH: 19
<212> TYPE: DNA
<213> ORGANISM: Homo sapiens
<220> FEATURE:
<221> NAME/KEY: misc_feature
<223> OTHER INFORMATION: Reverse primer for CCL8

<400> SEQUENCE: 42
agacctcctt gccccgttt                                        19

<210> SEQ ID NO 43
<211> LENGTH: 24
<212> TYPE: DNA
<213> ORGANISM: Homo sapiens
<220> FEATURE:
<221> NAME/KEY: misc_feature
<223> OTHER INFORMATION: Forward primer for TGFB1

<400> SEQUENCE: 43
ctgctgaggc tcaagttaaa agtg                                  24

<210> SEQ ID NO 44
<211> LENGTH: 21
<212> TYPE: DNA
<213> ORGANISM: Homo sapiens
<220> FEATURE:
<221> NAME/KEY: misc_feature
<223> OTHER INFORMATION: Reverse primer for TGFB1

<400> SEQUENCE: 44
tgaggtatcg ccaggaattg t                                     21

<210> SEQ ID NO 45
<211> LENGTH: 20
<212> TYPE: DNA
<213> ORGANISM: Homo sapiens
<220> FEATURE:
<221> NAME/KEY: misc_feature
<223> OTHER INFORMATION: Forward primer for HBA2

<400> SEQUENCE: 45
gccctggaga ggatgttcct                                       20

<210> SEQ ID NO 46
<211> LENGTH: 19
<212> TYPE: DNA
<213> ORGANISM: Homo sapiens
<220> FEATURE:
<221> NAME/KEY: misc_feature
<223> OTHER INFORMATION: Reverse primer for HBA2

<400> SEQUENCE: 46
cgtggctcag gtcgaagtg                                         19

<210> SEQ ID NO 47
<211> LENGTH: 23
<212> TYPE: DNA
<213> ORGANISM: Homo sapiens
<220> FEATURE:
<221> NAME/KEY: misc_feature
<223> OTHER INFORMATION: Forward primer for THBS1

<400> SEQUENCE: 47
cgtcacatag gctggaaaga ttt                                    23

<210> SEQ ID NO 48
<211> LENGTH: 24
<212> TYPE: DNA
<213> ORGANISM: Homo sapiens
<220> FEATURE:
<221> NAME/KEY: misc_feature
<223> OTHER INFORMATION: Reverse primer for THBS1

<400> SEQUENCE: 48
cactctaatg aaacccgtct ttgg                                   24

<210> SEQ ID NO 49
<211> LENGTH: 19
<212> TYPE: DNA
<213> ORGANISM: Homo sapiens
<220> FEATURE:
<221> NAME/KEY: misc_feature
<223> OTHER INFORMATION: Forward primer for ITGA2B

<400> SEQUENCE: 49
tgctgctgct caccatcct                                         19

<210> SEQ ID NO 50
<211> LENGTH: 19
<212> TYPE: DNA
<213> ORGANISM: Homo sapiens
<220> FEATURE:
<221> NAME/KEY: misc_feature
<223> OTHER INFORMATION: ITGA2B

<400> SEQUENCE: 50
ccggttccgc ttgaagaag                                         19

<210> SEQ ID NO 51
<211> LENGTH: 21
<212> TYPE: DNA
<213> ORGANISM: Homo sapiens
<220> FEATURE:
<221> NAME/KEY: misc_feature
<223> OTHER INFORMATION: Forward primer for PFKP

<400> SEQUENCE: 51
cctgtggcag agctgaagaa g                                      21

<210> SEQ ID NO 52
<211> LENGTH: 22
<212> TYPE: DNA
<213> ORGANISM: Homo sapiens
<220> FEATURE:
<221> NAME/KEY: misc_feature
<223> OTHER INFORMATION: Reverse primer for PFKP -continued

<400> SEQUENCE: 52
gcttgagcca ccactgttct tt                                    22

<210> SEQ ID NO 53
<211> LENGTH: 25
<212> TYPE: DNA
<213> ORGANISM: Homo sapiens
<220> FEATURE:
<221> NAME/KEY: misc_feature
<223> OTHER INFORMATION: Forward primer for FABP4

<400> SEQUENCE: 53
ggaaaatcaa ccaccataaa gagaa                                 25

<210> SEQ ID NO 54
<211> LENGTH: 21
<212> TYPE: DNA
<213> ORGANISM: Homo sapiens
<220> FEATURE:
<221> NAME/KEY: misc_feature
<223> OTHER INFORMATION: Reverse primer for FABP4

<400> SEQUENCE: 54
ggaagtgacg cctttcatga c                                     21

<210> SEQ ID NO 55
<211> LENGTH: 23
<212> TYPE: DNA
<213> ORGANISM: Homo sapiens
<220> FEATURE:
<221> NAME/KEY: misc_feature
<223> OTHER INFORMATION: Forward primer for LPL

<400> SEQUENCE: 55
cagcataatt cggaagggaa aac                                   23

<210> SEQ ID NO 56
<211> LENGTH: 24
<212> TYPE: DNA
<213> ORGANISM: Homo sapiens
<220> FEATURE:
<221> NAME/KEY: misc_feature
<223> OTHER INFORMATION: Reverse primer for LPL

<400> SEQUENCE: 56
gcacgatcat ctctctcaga gaaa                                  24